US008625093B2

(12) United States Patent
Yamaguchi et al.

(10) Patent No.: US 8,625,093 B2
(45) Date of Patent: Jan. 7, 2014

(54) PARTICLE CHARACTERIZATION DEVICE

(75) Inventors: Tetsuji Yamaguchi, Kyoto (JP); Tatsuo Igushi, Kyoto (JP); Takuji Kurozumi, Kyoto (JP)

(73) Assignee: Horiba, Ltd. (JP)

( * ) Notice: Subject to any disclaimer, the term of this patent is extended or adjusted under 35 U.S.C. 154(b) by 323 days.

(21) Appl. No.: 13/121,170

(22) PCT Filed: Sep. 25, 2009

(86) PCT No.: PCT/JP2009/066628
§ 371 (c)(1),
(2), (4) Date: Apr. 12, 2011

(87) PCT Pub. No.: WO2010/035775
PCT Pub. Date: Apr. 1, 2010

(65) Prior Publication Data
US 2011/0181869 A1  Jul. 28, 2011

(30) Foreign Application Priority Data

Sep. 26, 2008  (JP) ................. 2008-247412
Sep. 26, 2008  (JP) ................. 2008-247413
Sep. 26, 2008  (JP) ................. 2008-247414
Sep. 26, 2008  (JP) ................. 2008-247415
Aug. 31, 2009  (JP) ................. 2009-200046

(51) Int. Cl.
*G01N 15/02* (2006.01)
*G01N 21/00* (2006.01)
*G01J 4/00* (2006.01)

(52) U.S. Cl.
USPC .......... 356/336; 356/365; 356/341; 356/364; 356/370

(58) Field of Classification Search
USPC ............................. 356/335–344
See application file for complete search history.

(56) References Cited

U.S. PATENT DOCUMENTS 4,676,641 A * 6/1987 Bott .............................. 356/336
4,884,886 A * 12/1989 Salzman et al. .............. 356/367
(Continued)

FOREIGN PATENT DOCUMENTS

CN  1421686 A  6/2003
CN  101021523 A  8/2007
(Continued)

OTHER PUBLICATIONS

International Search Report for International Application No. PCT/JP2009/066628 mailed Dec. 22, 2009 with English translation.

(Continued)

*Primary Examiner* — Gregory J Toatley
*Assistant Examiner* — Jarreas C Underwood
(74) *Attorney, Agent, or Firm* — Cantor Colburn LLP

(57) ABSTRACT

Provided is a particle characterization device that can ensure measurement accuracy even though light detecting means has a single configuration, and enables the number of optical elements to be decreased as much as possible to suppress cost increase and reduce the number of adjustment places, and the particle characterization device has an incident side polarizer and an incident side ¼ wavelength plate as an illumination optical system mechanism and, as a light receiving optical system mechanism, an exit side ¼ wavelength plate and an exit side polarizer that can be rotated to a plurality of angle positions around a cell, wherein light attenuating means that prevents a polarization state from being changed is provided on a light path, and a light attenuation rate by the light attenuating means is controlled such that a detected light intensity at each measurement position falls within a measurement range of light detecting means.

12 Claims, 18 Drawing Sheets

(56) References Cited

U.S. PATENT DOCUMENTS

| | | | |
|---|---|---|---|
| 4,953,978 A * | 9/1990 | Bott et al. | 356/336 |
| 5,104,221 A * | 4/1992 | Bott et al. | 356/336 |
| 5,502,561 A * | 3/1996 | Hutchins et al. | 356/336 |
| 5,515,163 A * | 5/1996 | Kupershmidt et al. | 356/338 |
| 6,011,621 A * | 1/2000 | Marijnissen et al. | 356/336 |
| 6,091,492 A * | 7/2000 | Strickland et al. | 356/336 |
| 6,118,532 A * | 9/2000 | Peters | 356/338 |
| 6,407,812 B1 * | 6/2002 | Kurozumi et al. | 356/336 |
| 6,721,051 B2 * | 4/2004 | Menguç et al. | 356/368 |
| 6,774,994 B1 * | 8/2004 | Wyatt et al. | 356/337 |
| 7,602,482 B2 * | 10/2009 | Matsui | 356/237.3 |
| 2002/0057433 A1 | 5/2002 | Menguc et al. | |
| 2009/0010381 A1 * | 1/2009 | Schlomka | 378/7 |

FOREIGN PATENT DOCUMENTS

| | | |
|---|---|---|
| EP | 0190628 A2 | 8/1986 |
| EP | 0853760 A1 | 7/1998 |
| FR | 2279098 A1 | 2/1976 |
| JP | 60-011142 A | 1/1985 |
| JP | 61-193049 A | 8/1986 |
| JP | 63-70148 A | 3/1988 |
| JP | 4-278438 A | 10/1992 |
| JP | 8-128942 A | 5/1996 |
| JP | 11-514437 A | 12/1999 |
| JP | 2004-271287 A | 9/2004 |
| JP | 2004-317123 A | 11/2004 |
| JP | 2006-047166 A | 2/2006 |
| JP | 2007-322329 A | 12/2007 |
| JP | 2008-32548 A | 2/2008 |
| JP | 2008-39477 A | 2/2008 |
| WO | 97/13139 A1 | 4/1997 |
| WO | 02/25247 A2 | 3/2002 |

OTHER PUBLICATIONS

M. P. Menguc et al., "Characterization of size and structure of agglomerates and inhomogeneous particles via polarized light," International Journal of Engineering Science, 1998, vol. 36, p. 1569-p. 1593.

\* cited by examiner

PARTICLE CHARACTERIZATION DEVICE

This is a U.S. national stage application of International Application No. PCT/JP2009/066628, filed on 25 Sep. 2009. Priority under 35 U.S.C. §119(a) and 35 U.S.C. §365(b) is claimed from Japanese Application No. 2008-247412, filed 26 Sep. 2008, Japanese Application No. 2008-247413, filed 26 Sep. 2008, Japanese Application No. 2008-247414, filed 26 Sep. 2008, Japanese Application No. 2008-247415, filed 26 Sep. 2008, and Japanese Application No. 2009-200046, filed 31 Aug. 2009, the disclosure of each of which are also incorporated herein by reference.

TECHNICAL FIELD

The present invention relates to a particle characterization device that can measure physical properties related to a particle shape, particle size distribution, or the like, such as an aspect ratio or agglomeration level of particles (or a particle group) dispersed in a cell.

Further, the present invention relates to a particle characterization device that can measure shape-related physical property values such as not only a particle size but an aspect ratio and agglomeration level, and physical properties of particles such as a zeta potential on the basis of scattered light information.

BACKGROUND ART

In recent years, industrial demand for micro particles having various shapes is increased to thereby increase a market need for closely measuring physical properties of the micro particles, such as a particle size and shape.

For example, Patent literature 1 proposes a method and apparatus for measuring specific physical properties of micro particles on the basis of scattered light measurements using polarized light.

The apparatus described in Patent literature 1 is one that irradiates particles dispersed in a cell with polarized primary light such as laser light, and detects polarized light of scattered light of the primary light on a light receiving side to thereby measure a shape of the particles. According to the apparatus, on a light path from a light source to the cell, as illustrated in FIG. 1, optical elements are placed in the order of a convex lens 13, a polarizer 32, a half-wave retarder 33, a quarter-wave retarder 34, and also, before a light receiving element, optical elements are placed in the order of a half-wave retarder 35, a polarizer 36, and a convex lens 17.

In particular, in Patent literature 1, a light receiving optical system mechanism is configured to be rotatable around the cell, and adapted to be able to detect scattered light intensities having different angles with the single light receiving element. In the case of such a configuration, there are advantages of being able to facilitate a reduction in number of parts, and also of no instrumental error occurrence in the light receiving element in the dispersed in a cell with polarized primary light such as laser light, and detects polarized light of scattered light of the primary light on a light receiving side to thereby measure a shape of the particles. According to the apparatus, on a light path from a light source to the cell, as illustrated in FIG. 1, optical elements are placed in the order of a convex lens 13, a polarizer 32, a half-wave retarder 33, a quarter-wave retarder 34, and also, before a light receiving element, optical elements are placed in the order of a half-wave retarder 35, a polarizer 36, and a convex lens 17.

In particular, in Patent literature 1, a light receiving optical system mechanism is configured to be rotatable around the cell, and adapted to be able to detect scattered light intensities having different angles with the single light receiving element. In the case of such a configuration, there are advantages of being able to facilitate a reduction in number of parts, and also of no instrumental error occurrence in the light receiving element in the first place.

Meanwhile, a part where a light flux irradiated by the primary light and a detection angle based light flux on the light receiving side intersect with each other in the center of the cell corresponds to a part referred to as a scattering volume, and to arrange a pin hole having a diameter corresponding to the scattering volume before the detector to receive only scattered light is performed in this sort of particle characterization device. This is to enable the measurement to be performed at a high S/N ratio.

To cite above-described Patent literature 1, before the light receiving element, optical elements are placed in the order of a pin hole 19, a half-wave retarder 35, a polarizer 36, a convex lens 17, and a pin hole 31.

Meanwhile, in typical scattered light measurement, in order to detect intensities of a plurality of scattered lights that are scattered at different angles, a plurality of light receiving elements are provided; however, in Patent literature 1, the light receiving optical system mechanism is configured to be rotatable around the cell, and adapted to be able to detect scattered light intensities having different angles with the single light receiving element. In the case of such a configuration, there are advantages of being able to facilitate a reduction in number of parts, and also no instrumental error occurrence in the light receiving element in the first place.

Also, to configure the light receiving optical system mechanism to be rotatable, mechanical mechanism support parts such as a rail and a rotating plate are required in practice, and although some influence is present, the light receiving optical system mechanism itself is inevitably influenced by mechanical errors.

For this reason, there arises a problem that when the light receiving optical system is rotated to perform the measurements, at respective measurement angle positions, positions of a light flux of secondary light with respect to the pin hole are different, and detected light amounts at the respective measurement angle positions are varied.

However, in this sort of particle characterization device, depending on an angle and polarization direction of scattered light, scattered lights having an extremely wide intensity range from a very intense scattered light to a very weak scattered light may occur, and therefore the single light receiving element configuration as in Patent literature 1 may not cover the intensity range. Also, the apparatus described in Patent literature 1 uses a number of optical elements related to polarization and the like, which causes cost increase, and also many unexpected troubles may occur, such as a reduction in transmittance, occurrence of stray light, increase in number of adjustment places.

Also, in the case of measuring a particle size by a dynamic light scattering method, a preferred scattering angle depends on a concentration of a liquid sample, and in the case where the liquid sample concentration is low, 90° is preferable, whereas in the case where the liquid sample concentration is high, 180° is preferable; however, in the case of measuring the liquid sample concentration in advance, work becomes cumbersome, and in the case of a trace amount of sample, a loss of the sample also becomes a problem.

Further, in the case where the liquid sample concentration is extremely high, even if the measurement is performed at the scattering angle of 180°, a sufficient amount of scattered light cannot be received, which may make it difficult to perform the measurement with high accuracy.

Also, conventionally, regarding physical properties of nano particles, shape-related physical property values such as an aspect ratio (horizontal to vertical ratio) and an agglomeration level, a particle size, and a dispersion level are respectively measured by using separate analyzers, i.e., by observations using an electron microscope such as a scanning electron microscope (SEM) or an optical microscope, by the dynamic light scattering method, and by measuring a zeta potential.

However, to measure the respective physical property values with the separate analyzers, a sufficient amount of liquid sample is required, and in the case where an amount of the liquid sample is trace in the range of a few μm to a few tens μm, the amount of the sample is short, and therefore the required analyses may not be performed.

Also, in the case of using the electron microscope or optical microscope, the shape-related physical property values and particle size are calculated as image processing results; as measurement results for the case of using the particle size distribution measuring device, the particle size and particle size distribution are respectively presented as a numerical value and a histogram; and in the case of using a zeta potential measuring device, the zeta potential is presented as a numerical value or distribution. The zeta potential refers to a surface charge of a micro particle in a solution, i.e., a potential on a "sliding plane" on which liquid flow starts to occur in an electric double layer formed around the micro particle in the solution. In the case of the micro particle, as an absolute value of the zeta potential increases, repulsive force between the particles is increased to enhance stability of the particles. On the other hand, as the zeta potential approaches zero, the particles are likely to agglomerate. That is, depending on a charge amount (charge state) of the particles, stability of a dispersion state of the particles is varied, and therefore to control the agglomeration/dispersion of the micro particles in the solution and characterize the micro particles, an importance level of the zeta potential measurement is increased.

However, although results of such measurements can be easily interpreted if a measurer is familiar with principles of the devices, it may be difficult for one unfamiliar with the measurements to interpret meanings of obtained numerical values and distributions.

[Patent literature 1] U.S. Pat. No. 6,721,051
[Patent literature 2] JP 2004-317123 A
[Patent literature 3] JP 2004-271287 A

SUMMARY OF INVENTION

Technical Problem

Therefore, a first aspect of the present invention is intended to provide a particle characterization device that can, even though a light receiving element (light detecting means) has a single configuration, ensure measurement accuracy, and enables the number of optical elements to be reduced as much as possible to thereby suppress cost increase, reduce stray light and the number of adjustment places, and achieve other advantages.

Also, a second aspect of the present invention is intended to provide a particle characterization device that can, even though configured to rotate a single light receiving element (light detecting means) to perform a measurement, suppress a variation in light amount at each measurement angle position, and keep an S/N ratio high to ensure measurement accuracy.

Further, a third aspect of the present invention is intended to provide a particle characterization device that can measure values of physical properties of particles, including a particle size, with high accuracy.

Still further, the fourth aspect of the present invention is intended to provided a particle characterization device that enables even one unfamiliar with measurements of various physical properties of particles to directly and easily understand measurement results through visual perception.

Solution to Problem

That is, a particle characterization device according to the first aspect of the present invention includes: a transparent cell that contains a sample in which a micro particle is dispersed in a dispersion medium; an illumination optical system mechanism having an incident side polarizer and an incident side ¼ wavelength plate that are sequentially provided on a light path from a light source to the cell arrived by primary light emitted from the light source; a light receiving optical system mechanism that has: light detecting means adapted to detect an intensity of received light; and an exit side ¼ wavelength plate and an exit side polarizer that are sequentially provided on a light path through which secondary light scattered by the particle in the cell travels to the light intensity detecting means, and is rotatably supported around the cell; light attenuating means adapted to, without changing a polarization state of the primary light or the secondary light, attenuate the light with being able to change a light attenuation rate; an angle control part that controls the light receiving optical system mechanism to a plurality of rotational angle positions, and at each of the rotational angle positions, controls a polarization angle of the exit side polarizer to a plurality of angles; a light attenuation rate control part that controls the light attenuation rate by the light attenuating means such that a detected light intensity at each of the polarization angles at each of the rotational angle positions falls within a measurement range of the light detecting means; and a physical property calculation part that calculates a physical property of the particle on a basis of a light attenuation rate at each of the polarization angles at each of the rotational angle positions and a detected light intensity after the light attenuation.

If so, even though to be able to perform the measures even at a low concentration or on a micro particle, high sensitive light detecting means that can detect a low light intensity is used, intense light can be appropriately attenuated so as to meet a light intensity appropriate for the light detecting means, and therefore the single light detecting means can be used to measure physical properties with high accuracy over a wide range. Also, the number of optical elements that control polarization is only two, i.e., the ¼ λ plate and the polarizer for each of the incident and exit sides, and what are rotated to perform the measurements are only the exit side polarizer, and the incident and exit side ¼λ plates, so that the number of adjustment places can be reduced as much as possible to improve operability and measurement accuracy. Further, a transmittance and stray light can be prevented from being reduced and occurring, respectively.

Specific measurable physical properties include physical property values related to a particle shape, such as an aspect ratio and agglomeration level of a particle.

The light attenuating means may be one that can continuously change a light attenuation rate in a nonstep manner; however, in practice, it is only required to be able to change the light attenuation rate to a plurality of steps. For this purpose, the light attenuating means preferably includes: a plurality of ND filters respectively having different light attenuation rates; and a filter changing mechanism that selectively inserts any of the ND filters into the light path of the primary light or the secondary light.

Specific light attenuating means include one that includes a rotational holding plate arranged with the plurality of ND filters in a circumferential part, and is configured such that by rotating the rotational holding plate, any of the ND filters is positioned on the light path of the primary light or the secondary light.

To be able to measure even a transmitted light intensity with the light receiving optical system mechanism to simplify an optical system mechanism, the light receiving optical system mechanism is preferably configured to be able to be arranged on an extended line of the primary light transmitting through the cell to measure an intensity of transmitted light having transmitted through the cell by the light detecting means.

According to the present invention, the illumination optical system mechanism and light receiving optical system mechanism that are used to measure a particle shape can be directly used to measure also a particle size distribution. In such a case, a static particle size distribution measuring method that by changing an angle position of the light receiving optical system mechanism to measure an intensity distribution of scattered lights (secondary lights) at a plurality of angles, calculates a particle size distribution can be applied, or alternatively a dynamic particle size distribution measuring method that on the basis of a fluctuation in light intensity detected in the light detecting means, calculates a particle size distribution can also be applied. In the case of the dynamic particle size distribution measuring method, essentially, it is not necessary to change the angle position of the light receiving optical system mechanism, and also in the case of using a photon correlation method that obtains autocorrelation from a time-series change in number of photons of detected secondary light, and measuring a particle size distribution, a reference optical system is also not required, so that the particle size distribution can be reasonably measured.

In the case of applying the dynamic particle size distribution measuring method, to be able to ensure measurement accuracy even if a concentration is changed, more preferably, the rotational angle position of the light receiving optical system mechanism is configured to be changed depending on a particle concentration in the sample.

Also, a particle characterization device according to the second aspect of the present invention includes: a transparent cell that contains a sample in which a micro particle is dispersed in a dispersion medium; an illumination optical system mechanism having an incident side polarizer and an incident side ¼ wavelength plate that are sequentially provided on a light path from a light source to the cell arrived by primary light emitted from the light source; a light receiving optical system mechanism that has: light detecting means adapted to detect an intensity of received light; and an exit side ¼ wavelength plate and an exit side polarizer that are sequentially provided on a light path through which secondary light scattered by the particle in the cell travels to the light intensity detecting means, and is rotatably supported around the cell; an angle control part that rotates the light receiving optical system mechanism around the cell to control the light receiving optical system mechanism to a plurality of rotational angle positions, and at each of the rotational angle positions, controls a polarization angle of the exit side polarizer to a plurality of angles; a correction parameter storage part that stores a correction parameter for a detected light intensity at each of the measurement angle positions; and a physical property calculation part that, on a basis of a sample detected light intensity corresponding to a detected light intensity at each of the polarization angles at each of the measurement angle positions and the correction parameter, calculates a physical property related to a shape of the particle.

If so, correction parameters are set for the respective measurement angle positions, and therefore variations in light amount due to mechanical errors at the respective measurement angle positions, or the like can be corrected by using the respective correction parameters, so that a physical property related to a particle shape can be measured with high accuracy. Also, in particular, without requiring a complicated mechanism, realization with a simple configuration is possible.

As the correction parameter, it is only necessary to use a detected light intensity that is obtained at each of the measurement angle positions by irradiating the cell in a non particle state with the primary light. If so, a configuration can also be easily provided such that for each sample measurement, the correction parameter is updated to be able to also respond to a variation with time, or the like.

On the other hand, to decrease a position displacement of a light flux of the secondary light with respect to a pin hole as much as possible to suppress a variation in detected light amount at each of the measurement angle positions in the first place, it is only necessary to, in the light receiving optical system mechanism, provide a slit, which extends in a direction perpendicular to a rotational plane of the light receiving optical system mechanism, in front of the light detecting means. The above-described actual mechanical displacement at each of the measurement angle positions appears in the direction perpendicular to the rotational plane of the light receiving optical system mechanism, and therefore in the case of the above slit, the scattered light can be surely passed through even if the mechanical displacement is present.

To be able to measure a physical property of a particle with accuracy over a wide range even though using the single light detecting means, light attenuating means adapted to, without changing a polarization state of the primary light or the secondary light, attenuate the light with being able to change an amount of the light; and a light attenuation rate control part that controls a light attenuation rate by the light attenuating means such that the detected light intensity at each of the polarization angles at each of the measurement angle positions falls within a measurement range of the light detecting means are preferably provided.

To be able to measure even a transmitted light intensity with the light receiving optical system mechanism to thereby simplify an optical system mechanism, the light receiving optical system mechanism is preferably configured to be able to be arranged on an extended line of the primary light transmitting through the cell to measure an intensity of transmitted light having transmitted through the cell by the light detecting means.

The light attenuating means may be one that can continuously change the light attenuation rate in a nonstep manner; however, in practice, it is only required to be able to change the light attenuation rate to a plurality of steps. For this purpose, the light attenuating means preferably includes: a plurality of ND filters respectively having different light attenuation rates; and a filter changing mechanism that selectively inserts any of the ND filters into the light path of the primary light or the secondary light.

Further, a particle characterization device according to the third aspect of the present invention is one that has: a cell that contains a liquid sample in which a particle is dispersed; a light source that irradiates the particle in the cell with light;

and a light receiving part that receives scattered light emitted from the particle irradiated with the light, and on the basis of scattered light information serving as information on the scattered light, measures a physical property of the particle, includes at least: a particle size measuring mechanism that uses a dynamic light scattering method to measure a particle size of the particle; and a transmitted light amount measuring mechanism that measures, among lights irradiated from the light source, an amount of transmitted light having transmitted through the liquid sample contained in the cell, and further includes a light receiving position moving mechanism that on the basis of the amount of the transmitted light, moves a light receiving position for the scattered light in the particle size measuring mechanism.

Specifically, the light receiving position moving mechanism includes a rotating mechanism and a sliding mechanism.

The particle characterization device according to the present invention can measure, among the lights irradiated from the light source, the amount of the transmitted light having passed through the liquid sample contained in the cell by the transmitted light amount measuring mechanism; however, the transmitted light amount is a value correlated to a concentration of the liquid sample, and therefore the transmitted light amount can be used to control the light receiving position for the scattered light at the time of measuring the particle size. That is, in the case of measuring the particle size on the basis of the dynamic light scattering method, it is preferable to, in the case where the liquid sample concentration is low, receive scattered light at a scattering angle of near 90°, and in the case where the liquid sample concentration is high, receive scattered light at a scattering angle of near 180°; however, in the present invention, a transmitted light amount of light can be preliminarily measured to figure out a concentration of the liquid sample from the transmitted light amount, and therefore, by using information on the concentration, at the time of measuring the particle size on the basis of the dynamic light scattering method, the scattering angle of near 90° or near 180° can be selected according to whether the concentration is high or low. Also, in the case where the liquid sample concentration is extremely high, it is difficult to receive a sufficient amount of scattered light; however, in the present invention, a light receiving distance for scattered light (a focus position of the light receiving part) can be moved so as to be able to receive an optimum amount of scattered light.

Accordingly, if so, scattered light can be received constantly at an optimum position independently of whether the liquid sample concentration is high or low, and therefore the particle size can be measured with high accuracy.

In the case where the particle characterization device according to the present invention further includes a shape-related physical property value measuring mechanism that uses pluralities of polarizers, ¼ wavelength plates, and ½ wavelength plates to irradiate the liquid sample with lights having different polarization patterns, and on the basis of transmittances for the lights and a scattered light intensity ratio at a predetermined scattering angle, measures a shape-related physical property value of the particle, the shape-related physical property value measuring mechanism may double as the transmitted light amount measuring mechanism. The shape-related physical property value measuring mechanism measures a light transmittance at the time of measuring the shape-related physical property value; however, the transmittance is a value correlated to a transmitted light amount, so that the liquid sample concentration can be figured out even from the transmittance to control the light receiving position for scattered light at the time of measuring the particle size.

Preferably, the particle characterization device according to the present invention further includes, in addition to the above configuration, a zeta potential measuring mechanism, and includes: a measurement control part that controls the respective measuring mechanisms such that respective physical property values of the shape-related physical property value, the particle size, and a zeta potential are measured in this order.

If so, the shape-related physical property value is first measured, and therefore a light transmittance of the liquid sample measured during the measurement can be used to control the light receiving position for scattered light at the time of measuring the particle size. Also, in order to measure the zeta potential by an electrophoresis method, it is necessary to insert electrodes into the cell to apply a voltage; however, the voltage application may cause a state of the particle, or the electrode insertion may cause the liquid sample to overflow or be lost from the cell. However, by measuring the zeta potential last, the particle state change, the liquid sample loss, or the like by the zeta potential measurement does not influence the measurements of the other physical property values, so that the respective physical property values can be accurately measured with the one device, and even a trace amount of liquid sample can be sufficiently analyzed.

Also, a particle characterization device according to the fourth aspect of the present invention is one including at least: a shape-related physical property value measuring mechanism that obtains an aspect ratio, an agglomeration level, and the like of a particle dispersed in a liquid sample; a particle size measuring mechanism that measures a particle size of the particle; and a zeta potential measuring mechanism that measures a zeta potential of the particle, and further includes an image data generation part that generates: particle image data for, on the basis of pieces of measurement result data in the shape-related physical property value measuring mechanism and the particle size measuring mechanism, displaying a particle surface shape and the particle size as an image; and zeta potential image data for, on the basis of measurement result data in the zeta potential measuring mechanism, displaying the zeta potential of the particle as a size of a layer from a particle surface of the particle and/or a color of the layer from the particle surface.

If so, on the basis of the measurement results obtained as numerical values and the like, such as the shape-related physical property values and particle size, the image of the particle in the liquid sample is generated, so that from the embodied measurement results, the state of the particle in the liquid sample can be sterically and sensuously figured out and even one unfamiliar with the measurements can easily understand the measurement results. Also, the layer representing the electric field is displayed as the layer, and the size or color of the layer representing the electric field is displayed with being changed depending on the zeta potential measurement result, so that the zeta potential measurement result can be easily figured out at a glance and an understanding level is improved. In the circumference (outer edge) of the particle in the pieces of particle image data obtained on the basis of the measurement results of the shape-related physical property values, particle size, and the like, data on the electric field (zeta potential image data) obtained on the basis of the zeta potential measurement result is displayed, so that even one unfamiliar with the measurements is likely to understand a state of the micro particle in the solution. Further, the measurements of the various types of physical properties are performed in the liquid, and therefore the state of the particle, which cannot be known from a dry state observation image by an electron microscope such as a SEM, can be specifically figured out.

Note that, in the present invention, regarding the change in color, only any attribute of hue, lightness, and saturation may change, or the three color attributes may change in combination.

In order for the size or color of the layer representing the electric field to be changed depending on the zeta potential measurement result, preferably, the particle characterization device further includes a table storage part that stores a table in which the measurement result data in the zeta potential measuring mechanism, and the size of the layer from the particle surface and/or the color of the layer from the particle surface are related to each other.

Advantageous Effects of Invention

According to the first aspect of the present invention configured as described, at the time of detecting a light intensity, light is appropriately attenuated by the light attenuating means, and thereby even with the single light detecting means, the physical properties can be measured with high accuracy over a wide range. Also, the number of required optical elements is small, so that a transmittance and stray light can be prevented from being reduced and occurring, respectively, and also as an optical element that is rotationally driven for measurements, the exit side polarizer is only required, so that the number of adjustment places can be reduced as much as possible to improve operability and measurement accuracy.

Also, according to the second aspect of the present invention, because correction parameters are set for the respective measurement angle positions, light amount variations or the like due to mechanical errors at the respective measurement angle positions can be corrected with use of the correction parameters, and therefore the physical properties related to a particle shape can be measured with high accuracy. Also, without requiring a complicated mechanism, realization with a simple configuration is possible.

Further, according to the third aspect of the present invention, depending on a concentration of the liquid sample, the light receiving position for scattered light at the time of the particle size measurement can be moved to constantly receive the scattered light at an appropriate position, and therefore the particle size measurement can be performed with high accuracy. Also, by providing the shape-related physical property measuring mechanism, zeta potential measuring mechanism, and the like, even in the case of a trace amount of liquid sample, the various physical properties can be efficiently measured only with the one device.

Still further, according to a fourth aspect of the present invention, the measurement results of the various types of physical properties are displayed as an image together with numerical values and distribution, so that even one who measures various types of physical properties of particles for the first time, or does not have so many opportunities to perform measurements can figure out a particle's state of being in the liquid as a specific image, and therefore an understanding level for the measurement results of the various types of physical properties is improved.

DETAILED DESCRIPTION OF THE EMBODIMENTS

First Aspect of the Present Invention

In the following, one embodiment of a first aspect of the present invention is described with reference to the drawings.

A particle characterization device according to the present embodiment is one that measures physical properties related to a shape of particles, such as an aspect ratio and an agglomeration level, by irradiating the micro particles dispersed in a dispersion medium with polarized light and measuring an intensity angle distribution and polarization preservation levels in scattered lights of the polarized light.

Figure 1:
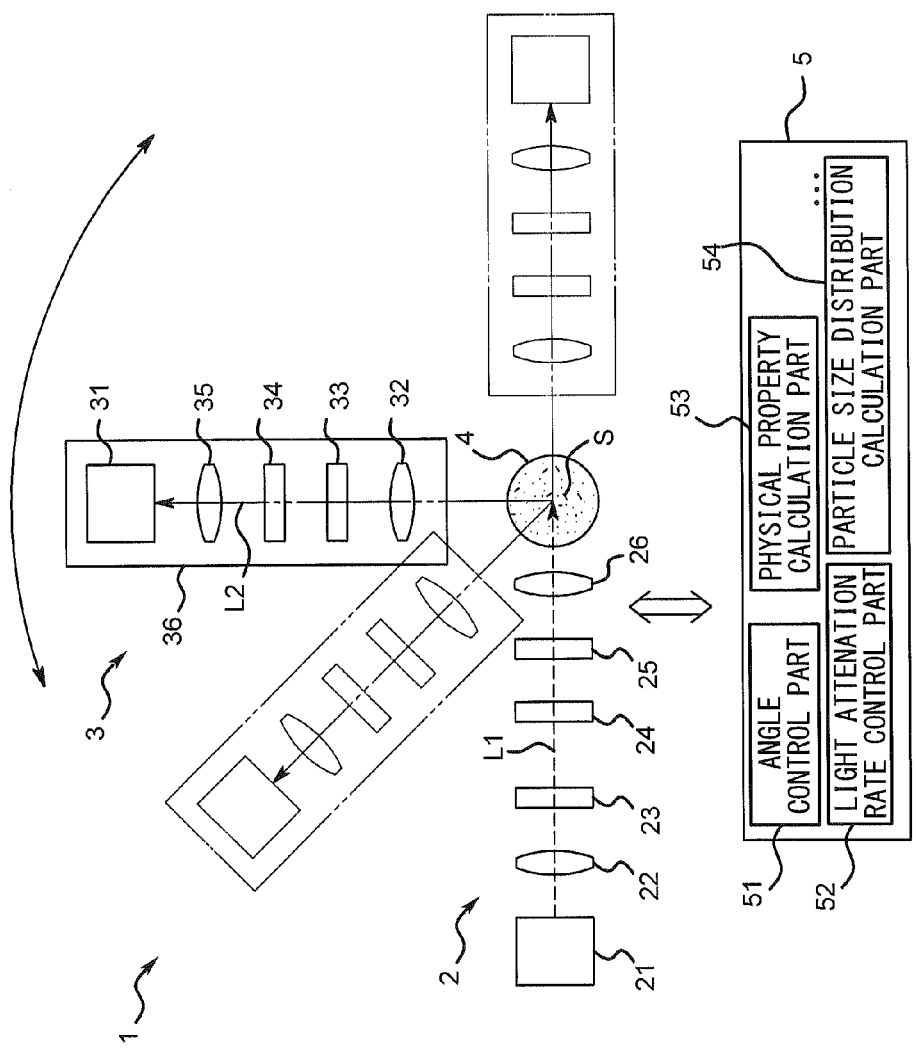
FIG. 1 is a schematic overall diagram illustrating an outline of a particle characterization device according to one embodiment of a first aspect of the present invention.

FIG. 1 illustrates an overall outline of the particle characterization device 1 as a schematic diagram. In the diagram, Reference numeral 2 represents an illumination optical system mechanism that irradiates a transparent cell 4 containing a sample with laser light L1 serving as primary light, and Reference numeral 3 represents a light receiving optical system mechanism that receives secondary light, i.e., scattered light L2 from micro particles S.

Figure 2:
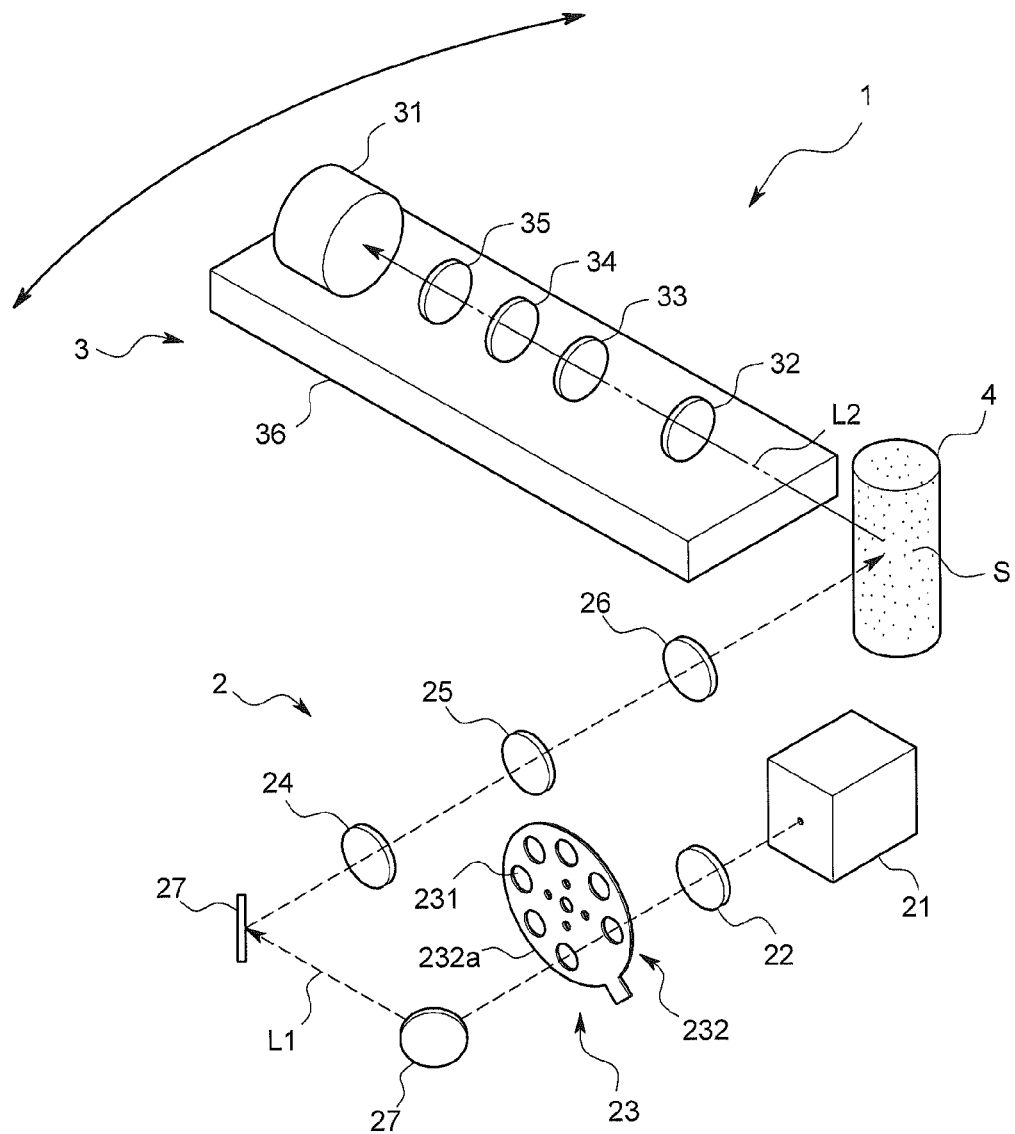
FIG. 2 is a schematic perspective view particularly illustrating light attenuating means in the same embodiment.

As illustrated in FIG. 2, the cell 4 can contain the sample inside which the micro particles S are dispersed in a dispersion medium. For example, the cell 4 is one having a hollow cylindrical body shape. Note that, in the present embodiment, a temperature adjustment mechanism (not illustrated) that can keep the cell 4 at a constant temperature is provided.

The illumination optical system mechanism 2 includes a semiconductor laser 21 serving as a light source, and a plurality of optical elements that pass the laser light L1 emitted from the semiconductor laser 21 therethrough to conduct it to the cell 4. Also, in the present embodiment, as the optical elements, a convex lens 22, light attenuating means 23, a polarizer 24 (hereinafter also referred to as an incident side polarizer 24), a ¼ wavelength plate 25 (hereinafter also referred to as an incident side ¼ wavelength plate 25), and a convex lens 26 are arranged in this order as viewed from the semiconductor laser 21.

As illustrated in FIG. 2, the light attenuating means 23 includes a plurality of ND filters 231 respectively having different light attenuation rates and a filter changing mechanism 232 that holds the ND filters 231. The ND filter 231 is a plate like one that attenuates light without changing a polarization state. The filter changing mechanism 232 is one including: a rotational holding plate 232*a* that holds the plurality of ND filters 231 in a circumferential part; and an unillustrated motor that rotationally drives the rotational holding plate 232*a*. Also, the light attenuating means 23 is configured such that by rotating the rotational holding plate 232*a* around the center of it, any of the ND filters 231 is positioned on a light path of the laser light L1.

Also, the illumination optical system mechanism 2 is provided with a plurality of reflective mirrors 27 for bending the light path on a semiconductor laser 21 side of the polarizer. This is because the reflective mirrors 27 change a polarization direction of light, and therefore after the polarization direction has been fixed, i.e., on the light path of the laser light L1 from the incident side polarizer 24 to the cell 4, any member that can change the polarization direction, such as the reflective mirror 27, is adapted not to be provided.

On the other hand, as illustrated in FIGS. 1 and 2, the light receiving optical system mechanism 3 includes: light detecting means 31 adapted to detect an intensity of received light; and a plurality of optical elements that conduct the scattered light L2 serving as the secondary light scatted by the micro particles S from the cell 4 to the light detecting means 31, and in the present embodiment, as the optical elements, a convex lens 32, a ¼ wavelength plate 33 (hereinafter also referred to as an exit side ¼ wavelength plate 33), a polarizer 34 (hereinafter also referred to as an exit side polarizer 34), and a convex lens 35 are arranged in this order as viewed from the cell 4. The light detecting means 31 is of a type that outputs the number of photons of the received light (or a photon number related value proportional to the number of photons, such as a voltage value), and for example, a photomultiplier is used in the present embodiment. The exit side polarizer 34 is configured to be rotatable around a light axis by an unillustrated motor or the like, and adapted to be able to extract a plurality of different polarization direction components of the scattered light L2 having passed through the ¼ wavelength plate.

Also, the light receiving optical system mechanism 3 is structured to be rotatable around the cell 4. Specifically, the light detecting means 31 and the respective optical elements are integrally supported by a base plate 36, and the base plate 36 is supported rotatably around the cell 4 by an unillustrated rotational support mechanism including a support shaft and an arc like rail.

Reference numeral 5 in FIG. 1 represents an information processor that controls a rotational angle position of the light receiving optical system mechanism 3 and a rotational angle of the exit side polarizer 34 around the light axis, i.e., controls a polarization angle, and also performs an analysis or the like of a shape on the basis of a detected light intensity by the light detecting means 31. The information processor 5 is one that is provided with a CPU, a memory, an A/D converter, and the like, and is configured to, according to a program stored in the memory, collaboratively operate the CPU and its peripheral devices to thereby fulfill functions as an after-mentioned angle control part 51, a light attenuation rate control part 52, a physical property calculation part 53, a particle size distribution calculation part 54, and the like.

Figure 3:
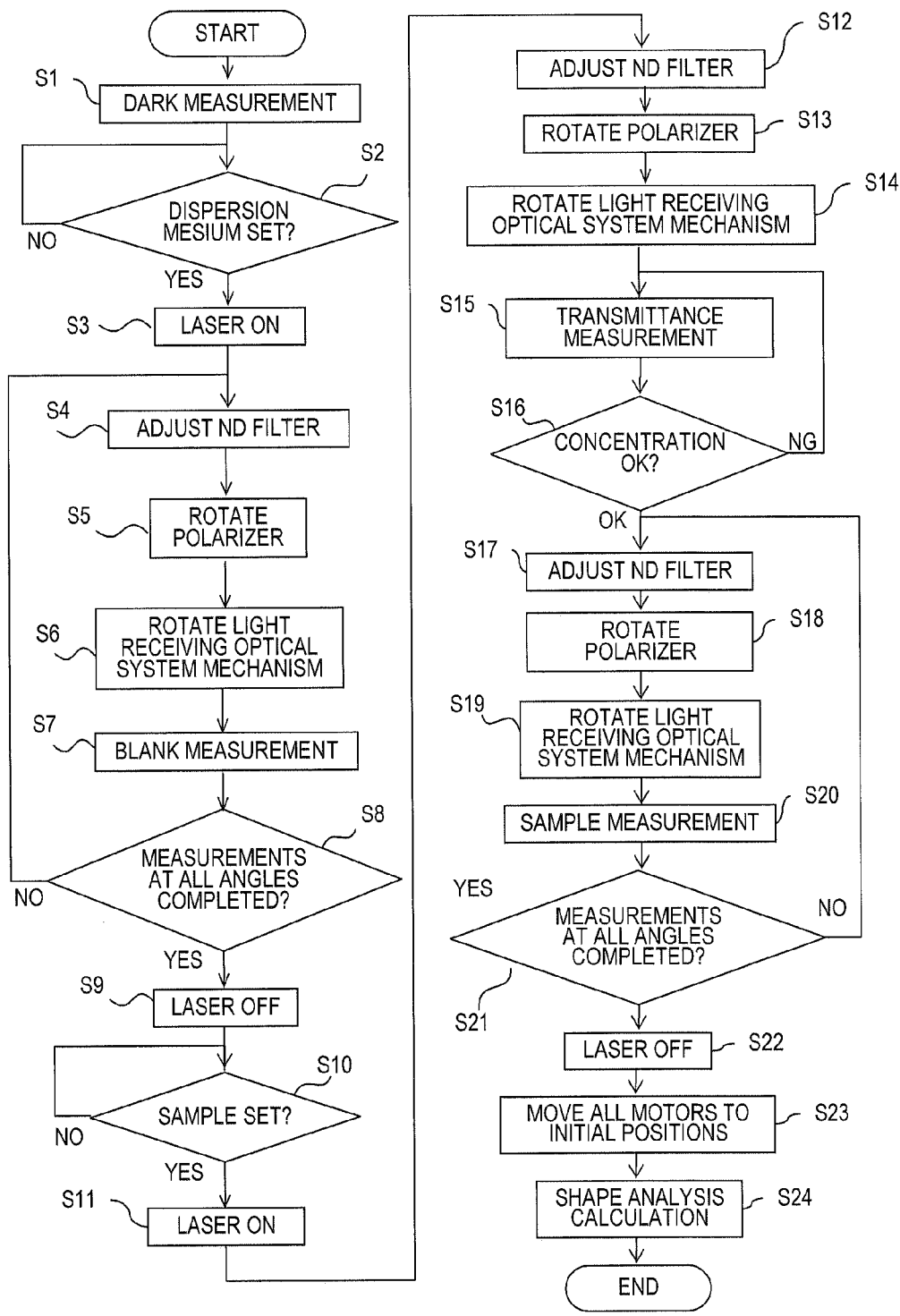
FIG. 3 is a flowchart illustrating operation of the particle characterization device in the same embodiment.

Next, operation of the particle characterization device 1 is described in detail with reference to a flowchart in FIG. 3, which also serves as an operational description of each of the parts in the information processor 5.

First of all, the information processor 5 performs a dark measurement (Step S1). The dark measurement refers to obtaining a light intensity detection value by the light detector in a nonillumination state. In this step, the rotational holding plate 232*a* is driven to position an area having no ND filter 231 on the light path of the laser light L1 to thereby make the rotational holding plate 232*a* function as a light shielding plate. Also, in this state, a signal from the light detecting means 31 is received to obtain the light intensity detection value in the nonillumination state. Note that the present embodiment is adapted to detect a light intensity by measuring the number of photons counted within a certain period of gate time.

Then, after the setting of the dispersion medium by an operator has been checked (Step S2), the information processor 5 performs a blank measurement (Steps S3 to S8). The blank measurement refers to containing, in the cell 4, a sample in which the dispersion medium is the same but no particle is present, and in this state, obtaining a light intensity detection value by the light detector. Here, the light receiving optical system mechanism 3 is set at a plurality of angle positions (e.g., 10° to 162° at 4° intervals), and also at each of the angle positions, the exit side polarizer 34 is set at a plurality of angles (e.g., Six angles at 15° intervals. Note that a predetermined reference angle is defined as 0°. The reference angle is made to substantially coincide with an original polarization angle of the semiconductor laser 21) to perform the blank measurement at each of the angles. That is, on the basis of the stepwise rotations of the light receiving optical system mechanism 3 and exit side polarizer 34, intensities of lights having a plurality of polarization components in each of scattered lights at the plurality of angles are respectively measured. Also, the light receiving optical system mechanism 3 is, as illustrated in FIG. 1, adapted to be rotatable to a position that squarely faces to the illumination optical system mechanism 2 and overlaps with the light axis of the laser light L1, i.e., a position where the light receiving optical system mechanism 3 can measure the laser light L1 having passed through the cell 4 (this angle position is defined as 0°), and in the blank measurement, by setting the angle position of the light receiving optical system mechanism 3 at 0°, a transmitted light intensity is also measured. Note that in the measurement of each of the light intensities, as described above, the number of photons counted within the certain period of gate time (or the photon number related value proportional to the number of photons, such as the voltage values) is measured; however, if it is determined that the number of photons exceeds a measurement range of the light detecting means 31 and is saturated, the rotational holding plate 232*a* is rotated to position an ND filter 231 having a higher light attenuation rate on the light path of the laser light L1 such that the number of photons falls within the measurement range of the light detecting means 31.

Subsequently, sample measurements are performed. That is, when the operator or the like puts in the cell 4 the sample in which particles are dispersed, and presses a start button or performs another operation (Step S10), the information processor 5 turns on the laser (Step S11), and also rotates the rotational holding plate 232a to position any of the ND filters 231 on the light path of the laser light L1 such that a detected light intensity falls within the measurement range of the light detecting means 31 (Step S12). Then, the polarizer is set at the reference angle, and also the light receiving optical system mechanism 3 is set at an angle position of 0° (Steps S13 and S14). Also, a transmittance at the time is calculated on the basis of the following expression (Step S15):

Transmittance=(1/Light attenuation rate of ND filter 231)×Detected light intensity in sample measurement/Detected light intensity in blank measurement If it is determined from the transmittance that a concentration exceeds a measurable concentration (Step S16), an indication that the concentration is too high is outputted to prompt the operator to adjust the concentration.

On the other hand, if it is determined that the concentration is within the measurable concentration range (Step S16), in the same manner as in the blank measurements, on the basis of the stepwise rotations of the light receiving optical system mechanism 3 and the exit side polarizer 34, intensities of lights having a plurality of polarization components in each of scattered lights at the plurality of angles are respectively measured with the light attenuation rate being appropriately controlled/adjusted so as to, in the same manner as that at the time of the blank measurements, meet the measurement range of the light detecting means (the functions as the angle control part 51 and the light attenuation rate control part 52, Steps S17 to S21).

Then, the respective parts are restored to an initial state, for example, the laser 21 is turned off (Steps S22 and S23), and also on the basis of the detected light intensities in the blank measurements and the detected light intensities in the sample measurements, which were measured at the respective rotational angle positions of the light receiving optical system mechanism 3 and the respective polarization angles of the exit side polarizer 34, the light attenuation rates in the respective measurements, and the like, a distribution related to a shape of the particles, in particular, to a horizontal to vertical ratio (aspect ratio or agglomeration level) is calculated (the function as the physical property calculation part 53, Step S24).

In addition, the present embodiment is configured to be able to also measure a particle size distribution based on the dynamic light scattering method with use of the same optical system mechanisms. The particle size distribution is calculated by the information processor 5 (the function as the particle size distribution calculation part 54). In the present embodiment, the particle size distribution of the particle group may be calculated by a photon correlation method, i.e., by generating autocorrelation data from time-series data on the number of received photons, and on the basis of the autocorrelation data, performing predetermined calculation processing; however, another method such as scattered light measurement based on a DC value may be employed.

Note that a preferable position (angle) for scattered light at the time of measuring the particle size (particle size distribution) depends on a concentration of the sample, and therefore the information processor 5 controls an angle position of the light receiving optical system mechanism 3 so as to, on the basis of the light transmittance of the sample measured at the time of measurements of the aspect ratio and/or agglomeration level, in the case where the transmittance is high (sample concentration is low), receive scattered light on a light path orthogonal to the laser light L1, i.e., 90° scattered light, and in the case where the transmittance is low (sample concentration is high), receive scattered light on the back side of the light path, i.e., scattered light having an angle exceeding 90°.

Thus, according to the particle characterization device 1 configured as described, cost reduction can be facilitated by simplification of the optical system, and also a transmittance and stray light can be suppressed from being reduced and occurring, respectively.

Also, because photons are counted, measurement sensitivity is improved, and therefore measurement accuracy for a trace amount of micro particles can be improved. On the other hand, because the measurement sensitivity is improved, highly intense light cannot be detected, and therefore a measurement range tends to narrow; however, by attenuating light with the ND filters, a wide measurement range can be ensured, which can also contribute to highly accurate measurements.

Further, the cell 4 can be adjusted in temperature, and therefore particles of which a size and shape are changed depending on temperature, such as a biomaterial or polymer, can be stably measured.

Also, even in the case of particles of which a particle size cannot be easily measured by a scattered light angle distribution, such as particles having a size of 100 nm or less, the particle size can be measured by the dynamic light scattering method, and for the measurements, the optical system mechanisms common to the shape measurements can be used.

Note that the first aspect of the present invention is not limited to the above embodiment.

For example, the light attenuating means may be inserted into any site if the site is on the light path of the primary or secondary light.

Second Aspect of the Present Invention

In the following, one embodiment of a second aspect of the present invention is described with reference to the drawings. Note that, in the following description, different points from the above embodiment according to the first aspect of the present invention are focused on to provide the description.

Figure 4:
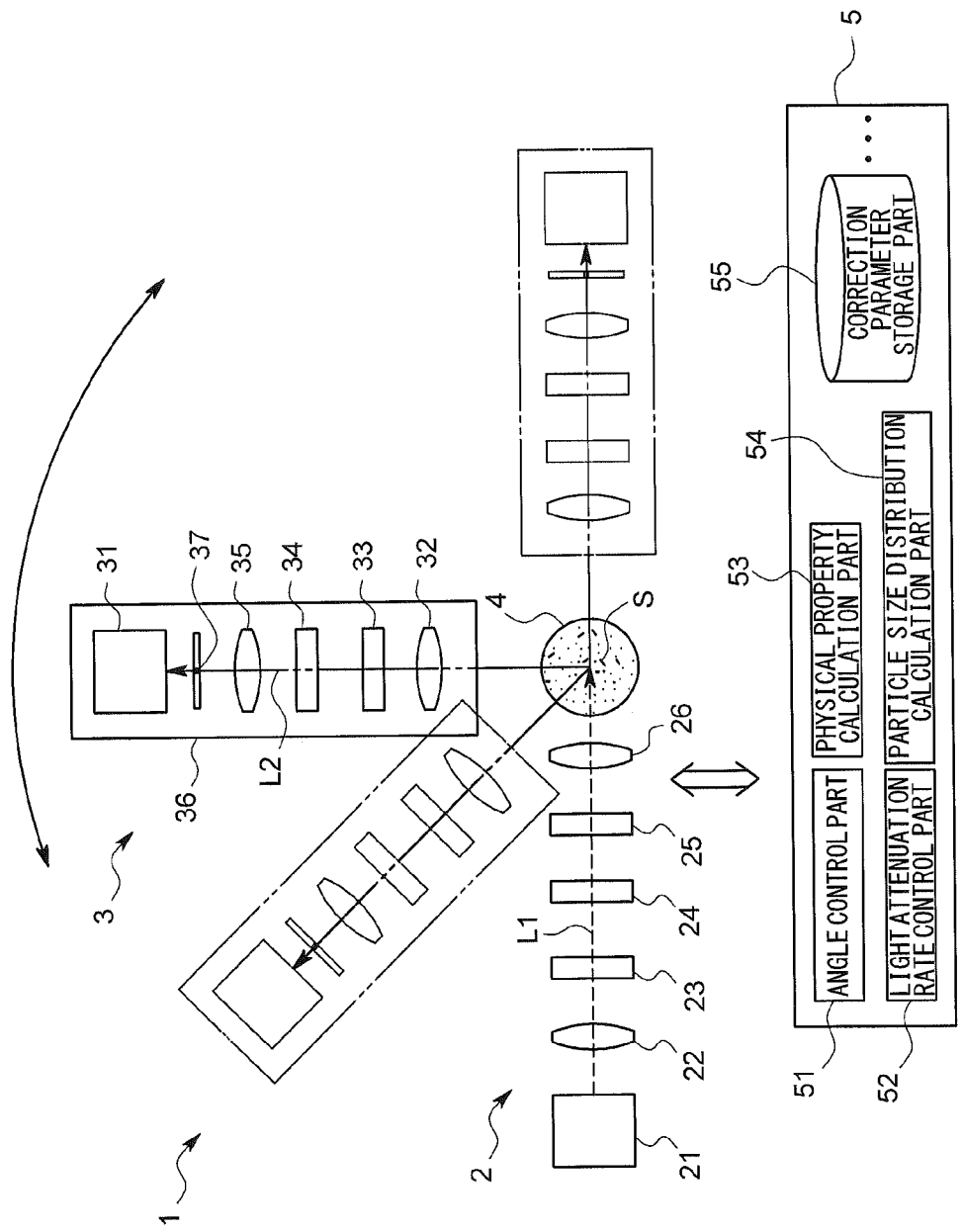
FIG. 4 is a schematic overall diagram illustrating an outline of a particle characterization device according to one embodiment of a second aspect of the present invention.

As illustrated in FIG. 4, optical elements in the present embodiment are the convex lens 32, the ¼ wavelength plate 33 (hereinafter also referred to as an exit side ¼ wavelength plate 33), the polarizer 34 (hereinafter also referred to as an exit side polarizer 34), the convex lens 35, and a slit 37 that are arranged in this order as viewed from a cell 4.

The slit 37 is a strip-shaped one that extends vertically to a rotational plane of a light receiving optical system mechanism 3, and a width of the slit 37 is set to a size corresponding to the above-described scattering volume. Also, a length of the slit 37 is longer than the width size, and set to a minimum size that can accommodate a position displacement of scattered light caused by mechanical errors to mostly pass the scattered light through the slit 37.

In the present embodiment, the respective detected light intensities in the above blank measurements serve as correction parameters for correcting the detected light intensities in the above sample measurements. The detected light intensities by the blank measurements are stored in a correction parameter storage part 55 that is set in the memory of the above information processor.

Here, an example of calculations for, on the basis of the detected light intensities in the blank measurements, correcting the detected light intensities obtained at the time of the sample measurements is described. In the case where the respective light intensities in the blank measurements are varied, all of which should have been expected to have the same value, it is thought that the variations are caused by position displacements between the slit 37 and the scattered lights at the respective measurement angles by the rotation of the light receiving optical system mechanism 3. Accordingly, a maximum value is extracted among the respective detected light intensities in the blank measurements, and by multiplying ratios of the respective detected light intensities in the blank measurements to the maximum value by the corresponding detected light intensities obtained at the time of the sample measurements, the corrections are made.

Thus, according to a particle characterization device 1 configured as described, for the respective polarization angles at the respective measurement angle positions, the blank measurements for corrections are performed, and from results of the measurements, the mechanical error based light amount variations or the like at the respective measurement angle positions are corrected, and therefore even with the single light detecting means 31, physical properties related to a particle shape can be measured with high accuracy.

In addition, the measurements can be made only with the single light detecting means 31, which contributes to cost reduction, and there is also produced a very significant effect that can, with the optical hardware being shared for the above shape measurements, even in the case of particles of which a particle size cannot be easily measured by a scattered light angle distribution, such as particles having a size of 100 nm or less, the particle size can be measured by the dynamic light scattering method.

Note that the second aspect of the present invention is not limited to the above embodiment.

For example, in the above embodiment, in the above embodiment, for the respective polarization angles at the respective measurement angle positions, the blank measurements for corrections are performed; however, the blank measurements is not performed for the respective polarization angles, but may be performed only at the respective measurement angles.

Also, it is not necessary to perform the blank measurements for each sample measurement, but in the case of the same type of sample or dispersion medium, an embodiment may be configured such that pieces of data obtained by performing the blank measurements are preliminarily stored in the correction parameter storage part, and values registered in the correction parameter storage part are used to correct respective detected light intensities obtained at the time of sample measurements.

Further, it should be appreciated that another calculation method for the corrections is possible.

Third Aspect of the Present Invention

First Embodiment

In the following, a first embodiment of a third aspect of the present invention is described with reference to the drawings.

Figure 5:
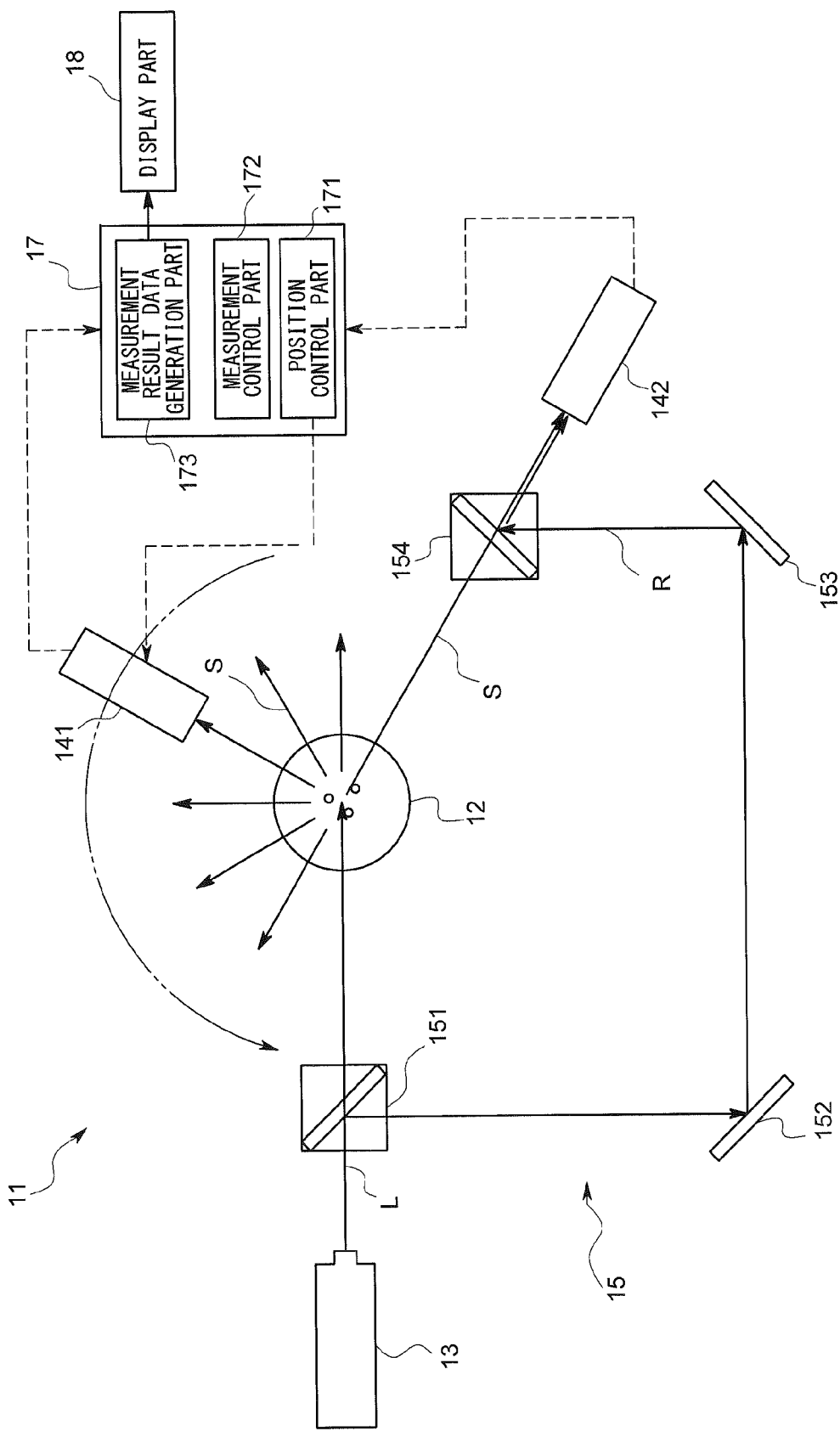
FIG. 5 is a schematic overall diagram illustrating an outline of a particle characterization device according to a first embodiment of a third aspect of the present invention.

FIG. 5 is a diagram illustrating an outline of a configuration of a particle characterization device 11 according to the present embodiment. The particle characterization device 11 according to the present embodiment is one provided with a measuring mechanism for shape-related physical property values such as an aspect ratio and/or an agglomeration level, a particle size measuring mechanism, a molecular weight measuring mechanism, and a zeta potential measuring mechanism, and as illustrated in FIG. 5, provided with: a cell 12 having a circle shaped cross section that is made of transparent quartz glass or the like and contains a liquid sample in which a particle group is dispersed in a dispersion medium such as water; a laser 13 that irradiates the liquid sample with laser light L; light receiving parts 141 and 142 respectively including photomultiplier tubes that receive scattered lights S emitted from the particle group in the liquid sample irradiated with the laser light L and output pulse signals corresponding to the numbers of photons of the scattered lights S or electrical signals corresponding to fluctuations of light intensities; a reference optical system 15 including a half mirror 151 that branches part of the laser light L emitted from the laser 13, mirrors 152 and 153, and a half mirror 154 that mixes reference light R from the mirror 153 and the scattered light S; a position control part 171 that controls a light receiving position for the scattered light S in the particle size measuring mechanism; a measurement control part 172 that controls respective parts such that measurements of respective physical property values are performed according to a predetermined sequence; and a measurement result data generation part 173 that generates pieces of data for collectively displaying measurement results of the respective physical property values as one report.

In the following, a configuration of each of the measuring mechanisms is described in more detail.

Figure 6:
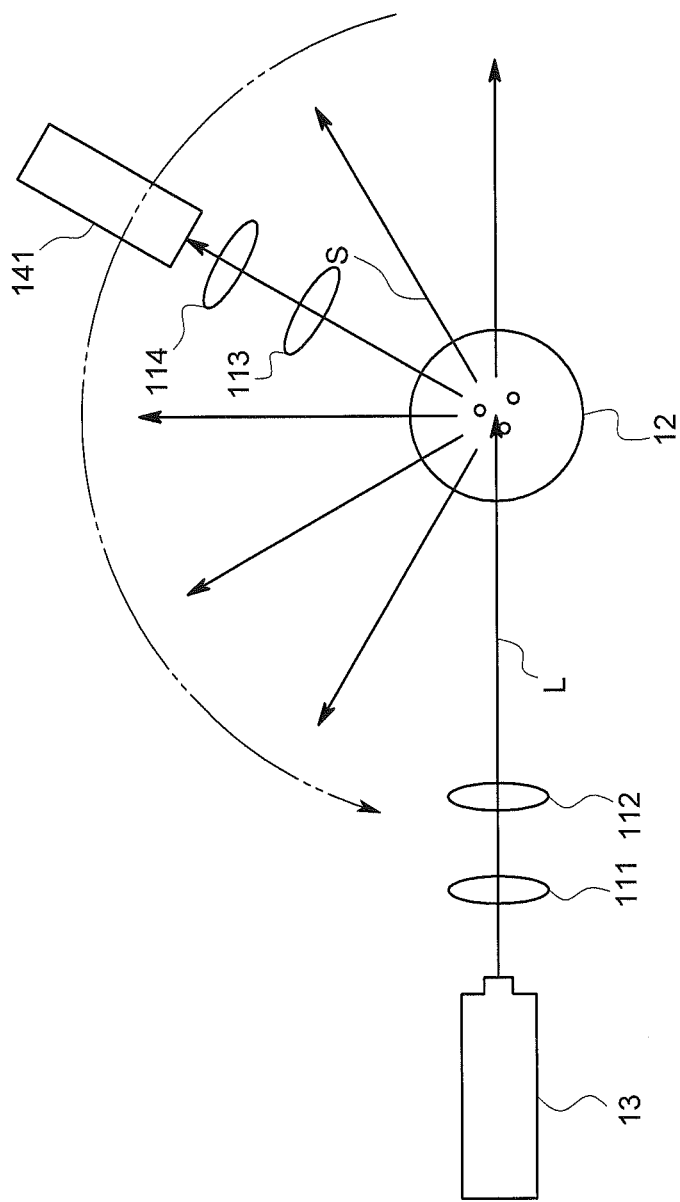
FIG. 6 is a schematic configuration diagram illustrating a shape-related physical property value measuring mechanism in the same embodiment.

The shape-related physical property value measuring mechanism that measures the shape-related physical property values such as the aspect ration and agglomeration level includes, as illustrated in FIG. 6, the laser 13, polarizers 11 and 14, ¼ wavelength plates 112 and 113, and the light receiving part 141. The polarizer 111 is fixed to generate specific linear polarization from the laser light L emitted from the laser 13; however, the ¼ wavelength plates 112 and 113 and the polarizer 114 are rotatable around a light axis; the ¼ wavelength plates 112 converts the linear polarization to elliptical polarization, whereas the ¼ wavelength plates 113 restores the elliptical polarization to the linear polarization; and the polarizer 114 extracts only light having a desired polarization direction.

To measure the shape-related physical property values, the method described in U.S. Pat. No. 6,721,051 is used to first measure a transmittance of the liquid sample in the cell 12 for the laser light L. Then, while rotating the ¼ wavelength plates 112 and 113 and the polarizer 114 around the light axis, the laser light L is emitted, and in polarization patterns having a plurality of modes, while changing a position (angle) of the light receiving part 141, intensities of the scattered light S at predetermined scattering angles are measured. Subsequently, predetermined calculation processing is performed on scattered light intensity ratios at the respective angles to thereby calculate the aspect ratio and/or agglomeration level. In the measurements of the shape-related physical property values using the polarizations, such as the aspect ratio and agglomeration level, unless the transmittance is equal to or more than a predetermined value (70%), accurate results cannot be obtained, and therefore the transmittance of the sample is measured prior to the measurements.

Figure 7:
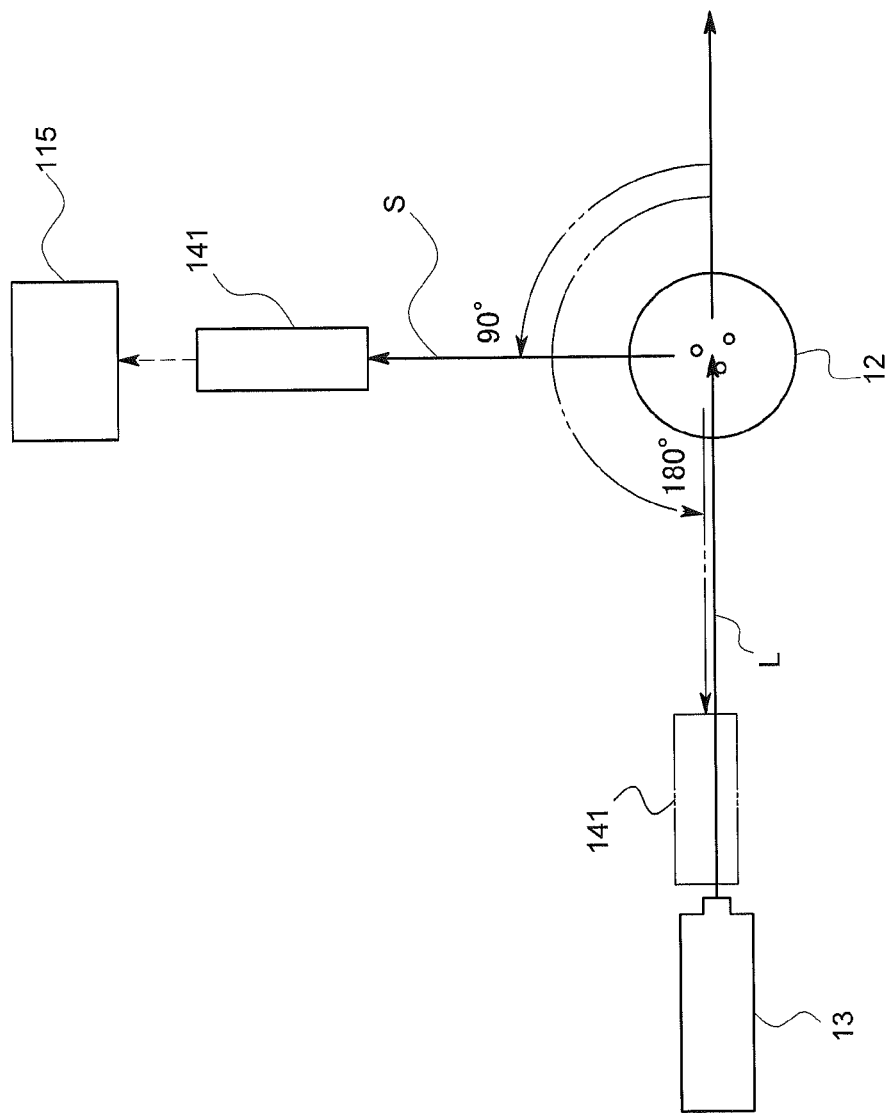
FIG. 7 is a schematic configuration diagram illustrating a particle size measuring mechanism in the same embodiment.

The particle size measuring mechanism includes, as illustrated in FIG. 7, the laser 13, the light receiving part 141, and a correlator 115. To measure a particle size (particle size distribution), the dynamic light scattering method is used, in which the liquid sample in the cell 12 is irradiated with the laser light L; the scattered light S emitted from the particle group in the liquid sample is received in the light receiving part 141; in the correlator 115 having received a pulse signal corresponding to the number of photons of the scattered light S from the light receiving part 141, autocorrelation data is generated from time-series data on the number of pulses of the pulse signal; and on the basis of the autocorrelation data, predetermined calculation processing is performed to thereby calculate the particle size distribution of the particle group. In the present embodiment, the calculation method based on the pulse signal corresponding to the number of photons is described in detail; however, the calculation is also possible from an electrical signal corresponding to a fluctuation in light intensity.

In the embodiment illustrated in FIG. 7, the light receiving part 141 receives the scattered light S through a light path orthogonal to the laser light L; however, a preferable position of the light receiving part 141 at the time of measuring the particle size (particle size distribution) depends on a concentration of the liquid sample. For this reason, the light receiving part 141 is provided with an unillustrated light receiving position moving mechanism. The light receiving position moving mechanism is specifically provided with: a stage (corresponding to a rotating mechanism) that is mounted thereon with the light receiving part 141 and rotatable with a predetermined radius around a predetermined position in the cell 12; and a rail member (corresponding to a sliding mechanism) that is provided on the stage and slidably supports the light receiving part 141 back and forth, and operations of the stage and rail member are controlled by the position control part 171.

Also, the position control part 171 rotates the stage mounted with the light receiving part 141 to control a light receiving angle of the light receiving part 141 so as to, according to the laser light transmittance of the liquid sample measured when the shape-related physical property values were measured, in the case where the transmittance is high (liquid sample concentration is low), receive the scattered light S through the light path orthogonal to the laser light L (scattering angle of 90°), and in the case where the transmittance is low (liquid sample concentration is high), receive the scattered light S through a light path substantially overlapping with the laser light L (scattering angle of near 180°). Note that the scattering angle for the case where the liquid sample concentration is high is near 180° as described above; however, for convenience of device arrangement, it is preferably 170 to 175°.

Further, in the case where the transmittance is extremely low (liquid sample concentration is extremely high), to be able to receive a sufficient amount of scattered light near the angle of 180°, the position control part 171 slides the light receiving part 141 on the stage through the rail member to control a focus position (a distance from the cell 12) of the light receiving part 141.

Figure 8:
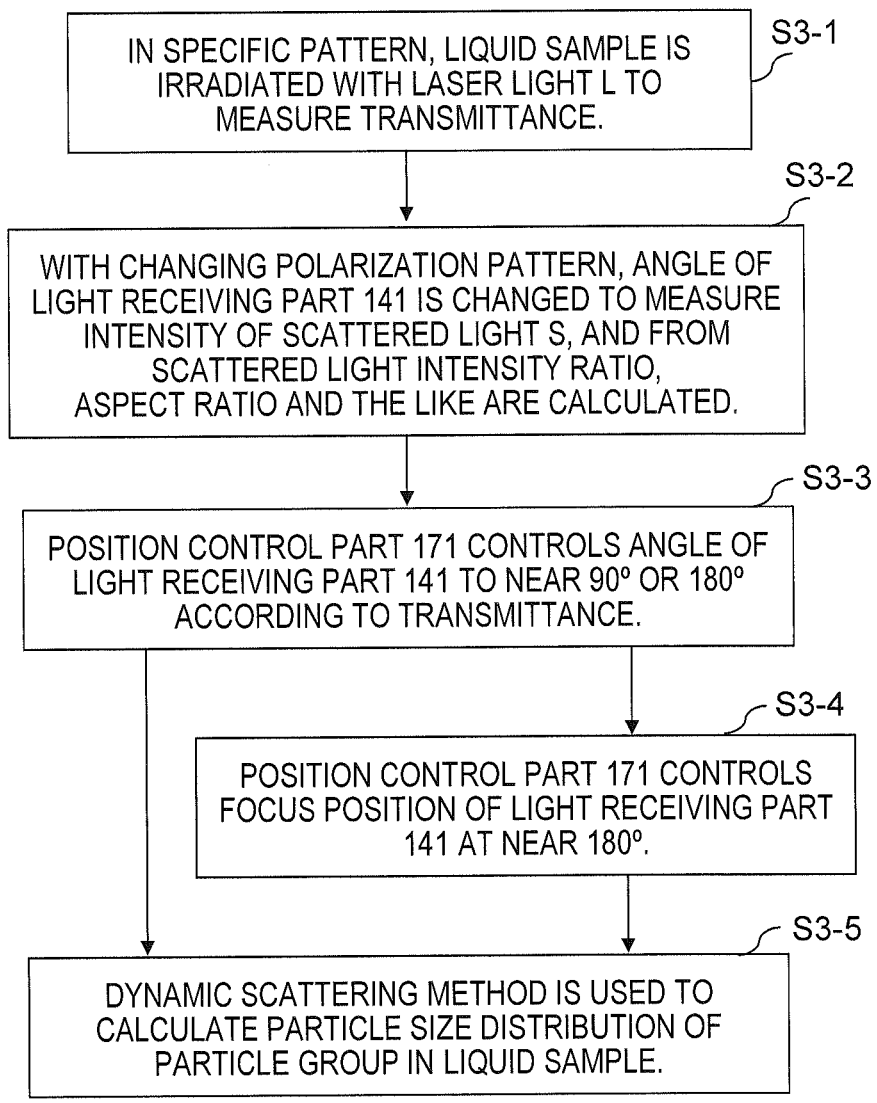
FIG. 8 is a flowchart illustrating a procedure for selecting a position for receiving scattered light to measure a particle size in the same embodiment.

A procedure for, as described, according to the laser light transmittance of the liquid sample obtained when the shape-related physical property values were measured, selecting the position for receiving the scattered light S to measure the particle size is described with reference to a flowchart in FIG. 8.

First, the polarizer 114 and the ¼ wavelength plates 112 and 113 are fixed; the liquid sample in the cell 12 is irradiated with the laser light L from the laser 13; and in a specific polarization pattern, the light receiving part 141 receives transmitted light to measure the transmittance for the laser light L (Step S3-1).

Then, while rotating the ¼ wavelength plates 112 and 113 and the polarizer 114 around the light axis, the liquid sample in the cell 12 is irradiated with the laser light L from the laser 13; in the polarization patterns respectively having the plurality of modes, while changing the position (angle) of the light receiving part 141, intensities of the scattered light S at the predetermined scattering angles are measured; and the predetermined calculation processing is performed on the basis of the scattered light intensity ratios at the respective angles to thereby calculate the aspect ratio and/or agglomeration level (Step S3-2).

Subsequently, the position control part 171 having obtained data on the laser light transmittance controls the angle of the light receiving part 141 so as to, according to the obtained laser light transmittance, in the case where the transmittance is high (liquid sample concentration is low), receive the scattered light S at the scattering angle of near 90°, and in the case where the transmittance is low (liquid sample concentration is high), receive the scattered light S at the scattering angle of near 180° (Step S3-3).

Further, in the case where the obtained laser light transmittance is extremely low (liquid sample concentration is extremely high), to receive a sufficient amount of scattered light S at the scattering angle of near 180°, the position (the distance from the cell 12) of the light receiving part 141 is controlled (Step S3-4).

Next, the dynamic light scattering method is used, in which the liquid sample in the cell 12 is irradiated with the laser light L; the scattered light S emitted from the particle group in the liquid sample is received in the light receiving part 141; in the correlator 115 having received a pulse signal corresponding to the number of photons of the scattered light S from the light receiving part 141, autocorrelation data is generated from time-series data on the number of pulses of the pulse signal; and on the basis of the autocorrelation data, the predetermined calculation processing is performed to thereby calculate the particle size distribution of the particle group in the liquid sample (Step S3-5).

Figure 9:
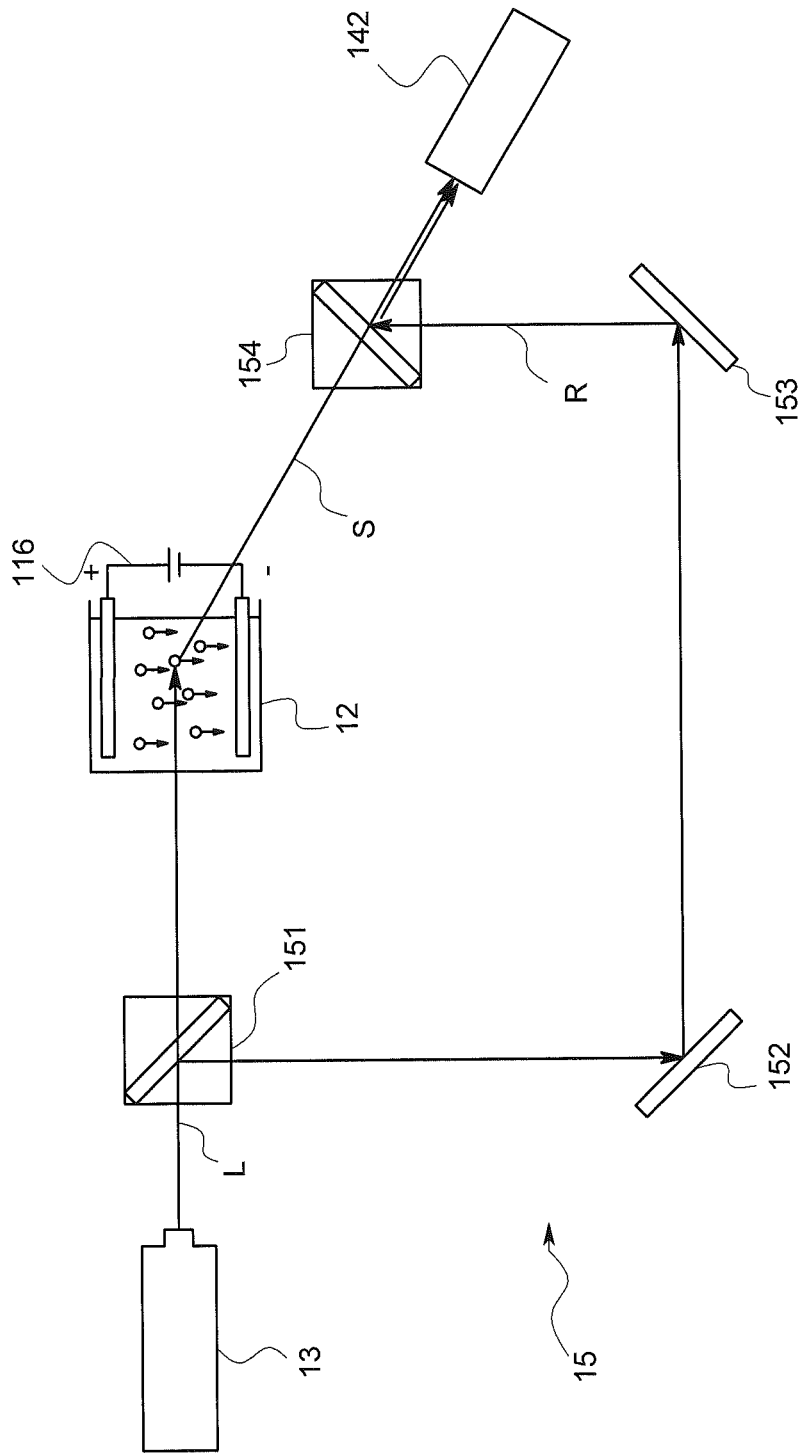
FIG. 9 is a schematic configuration diagram illustrating a zeta potential measuring mechanism in the same embodiment.

The zeta potential measuring mechanism includes, as illustrated in FIG. 9, the laser 13, a pair of electrodes 116 made of platinum or the like, the reference optical system 15, and the light receiving part 142. To measure the zeta potential, an electrophoresis method is used, in which with the electrodes inserted into the cell 12 being applied with a DC or AC voltage to apply an electric field to the particles in the liquid sample, the laser light L is irradiated to receive scattered light S scattered at a predetermined angle, and a difference in frequency (interference phenomenon) between the scattered light S and the reference light R is measured, whereby a moving speed of the particles in the liquid sample is calculated. Further, by performing predetermined calculation processing on the obtained moving speed, the zeta potential is calculated.

Figure 10:
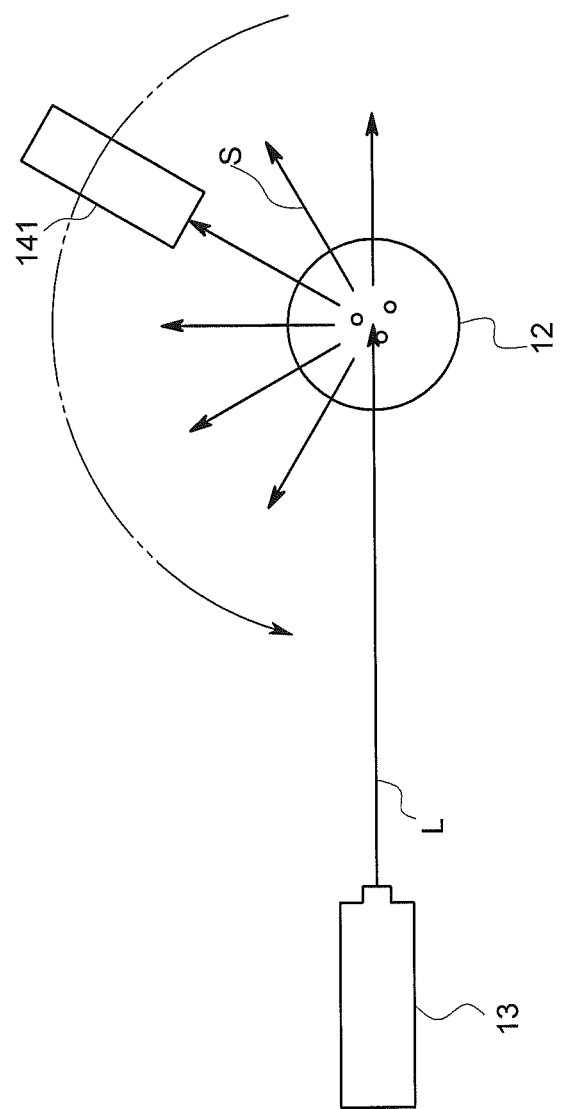
FIG. 10 is a schematic configuration diagram illustrating a molecular weight measuring mechanism in the same embodiment.

The molecular weight measuring mechanism includes, as illustrated in FIG. 10, the laser 13 and the light receiving part 141. To measure a molecular weight, a static optical scattering method is used, in which with use of a plurality of liquid samples respectively having different concentrations, while changing the position (angle) of the light receiving part 141, a liquid sample in the cell 12 is irradiated with the laser light L, and an angle distribution of the number of photons of scattered light S emitted from a particle group in the liquid sample is measured. Then, from a concentration of the liquid sample, and changes in scattered light amount based on the change in scattering angle, a Zimm plot is generated to calculate the molecular weight of the particle.

Figure 11:
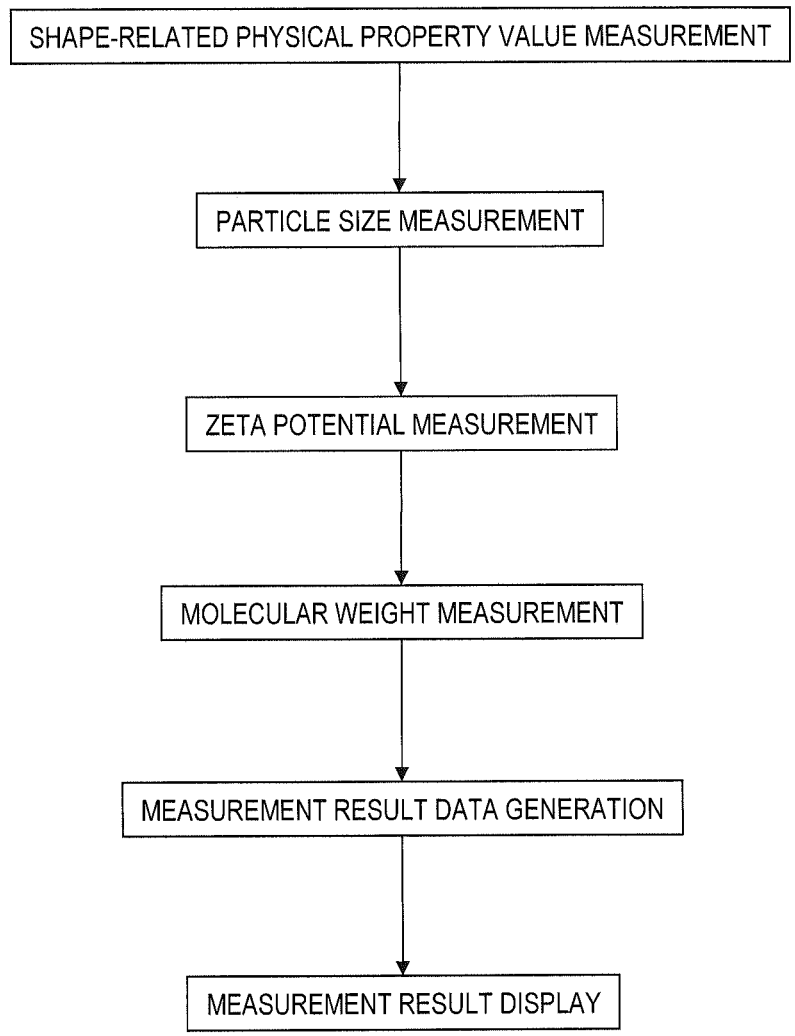
FIG. 11 is a flowchart illustrating a measurement sequence in the same embodiment.

In the present embodiment, a sequence for measuring these physical property values is controlled by the measurement control part 172, and as illustrated in FIG. 11, the shape-related physical property values, particle size, zeta potential, and molecular weight are continuously measured in this order.

Measurement results of the respective physical property values obtained on the basis of such a measurement sequence are transmitted to the measurement result data generation part 173, and edited into pieces of data for collectively displaying them as one report.

Note that respective functions of the position control part 171, the measurement control part 172, and the measurement result data generation part 173 are carried by the information processor 17 such as a computer, and by the CPU and its peripheral devices that collaboratively operate according to a predetermined program stored in a predetermined area of the memory of the information processor 17, the information processor 17 functions as the position control part 171, measurement control part 172, measurement result data generation part 173, and the like.

The pieces of measurement result data generated by the measurement result data generation part 173 are transmitted to a display part 18 provided with a display and the like, where the pieces of data are brought into the one report, which is then displayed. The display part 18 may be incorporated in the particle characterization device 11, or alternatively may be one connected with an external display.

According to the particle characterization device 11 configured as described, all of the measurements of the shape-related physical property values such as the aspect ratio and agglomeration level, particle size, zeta potential, and molecular weight can be performed on a liquid sample contained in the one cell 12, and therefore even in the case of a trace amount of liquid sample, sufficient analyses can be made.

Also, in the present embodiment, the shape-related physical property values such as the aspect ratio and agglomeration level are first measured, so that a light transmittance measured during the measurements is used to obtain a concentration of a liquid sample, and on the basis of the concentration, a light receiving angle of scattered light at the time of measuring the particle size can be controlled so as to, in the case where the liquid sample concentration is low, receive scattered light at a scattering angle of near 90°, and in the case where the liquid sample concentration is high, receive scattered light at a scattering angle of near 180°.

Further, in the case where the liquid sample concentration is extremely high, to receive a sufficient amount of scattered light at the scattering angle of near 180°, a light receiving distance for the scattered light at the time of measuring the particle size can be controlled.

Further, when in order to measure the zeta potential, a voltage is applied between the electrodes 116 in the cell 12, a particle state may be changed by the voltage application, or a liquid sample may be overflowed and lost from the cell 12 by the insertion of the electrodes 116; however, in the present embodiment, after the measurements of the shape-related physical property values and the particle size, the zeta potential is measured, and therefore the particle state change or the liquid sample loss by the zeta potential measurement does not influence the measurements of the other physical property values.

Second Embodiment

In the following, a second embodiment of the third aspect of the present invention is described with reference to the drawings, in which different points from the first embodiment are focused on to provide the description.

Figure 12:
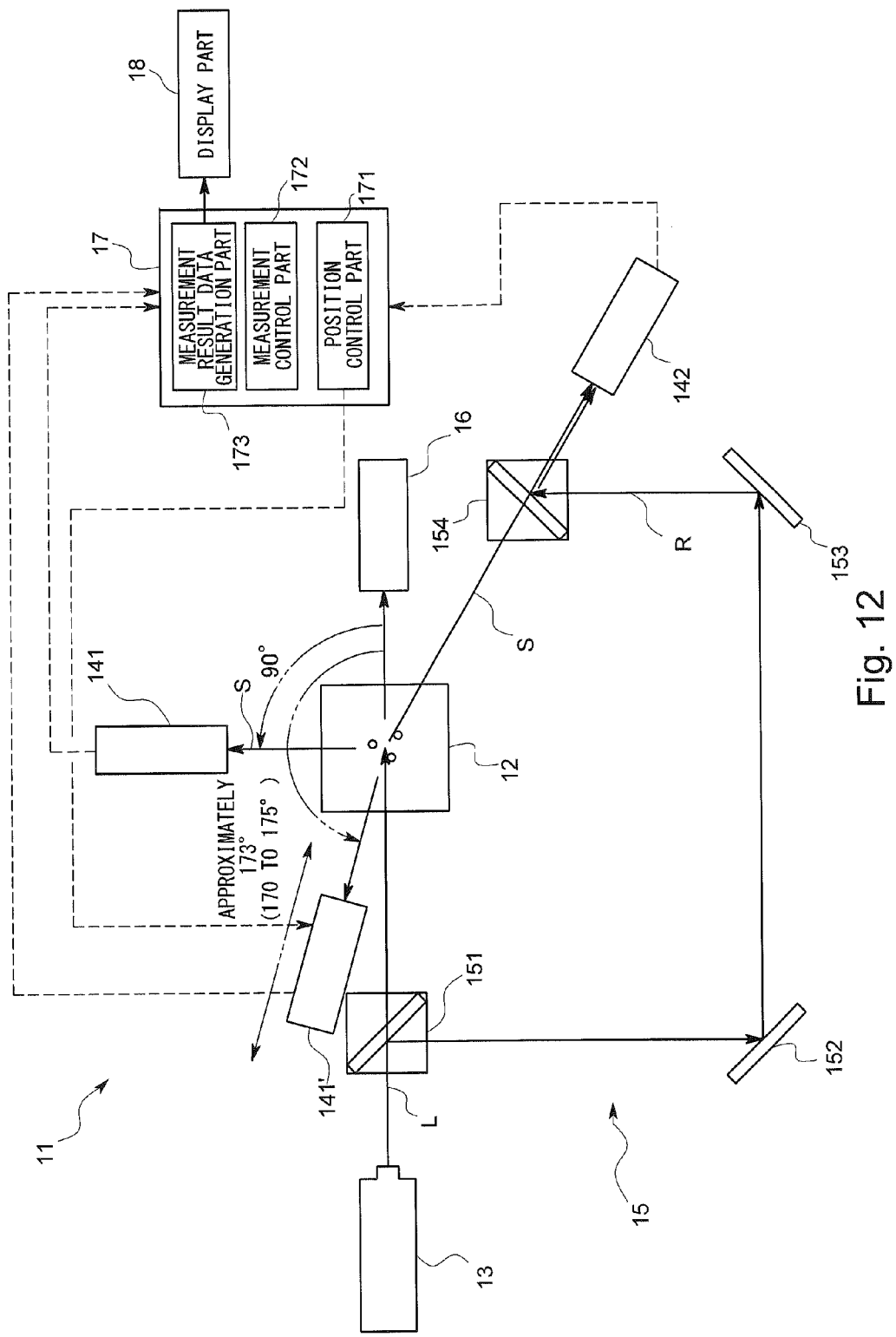
FIG. 12 is a schematic overall diagram illustrating an outline of a particle characterization device according to a second embodiment of the third aspect of the present invention.

FIG. 12 is a diagram illustrating an outline of a configuration of a particle characterization device 11 according to the present embodiment. The particle characterization device 11 according to the present embodiment is one provided with a particle size measuring mechanism, a molecular weight measuring mechanism, and a zeta potential measuring mechanism, of which, as illustrated in FIG. 12, a cell 12 has a square shaped cross section, and provided with: a light receiving part 141 that is provided to receive scattered light S at a scattering angle of near 90°; a light receiving part 141' that is provided to receive scattered light S at a scattering angle of near 180°; and a transmitted light amount measuring mechanism 6 including a transmitted light amount sensor. In addition, specifically, for convenience of device arrangement, the light receiving part 141' is preferably provided to receive scattered light S at a scattering angle of 170 to 175°, more specifically at a scattering angle of approximately 173°.

Figure 13:
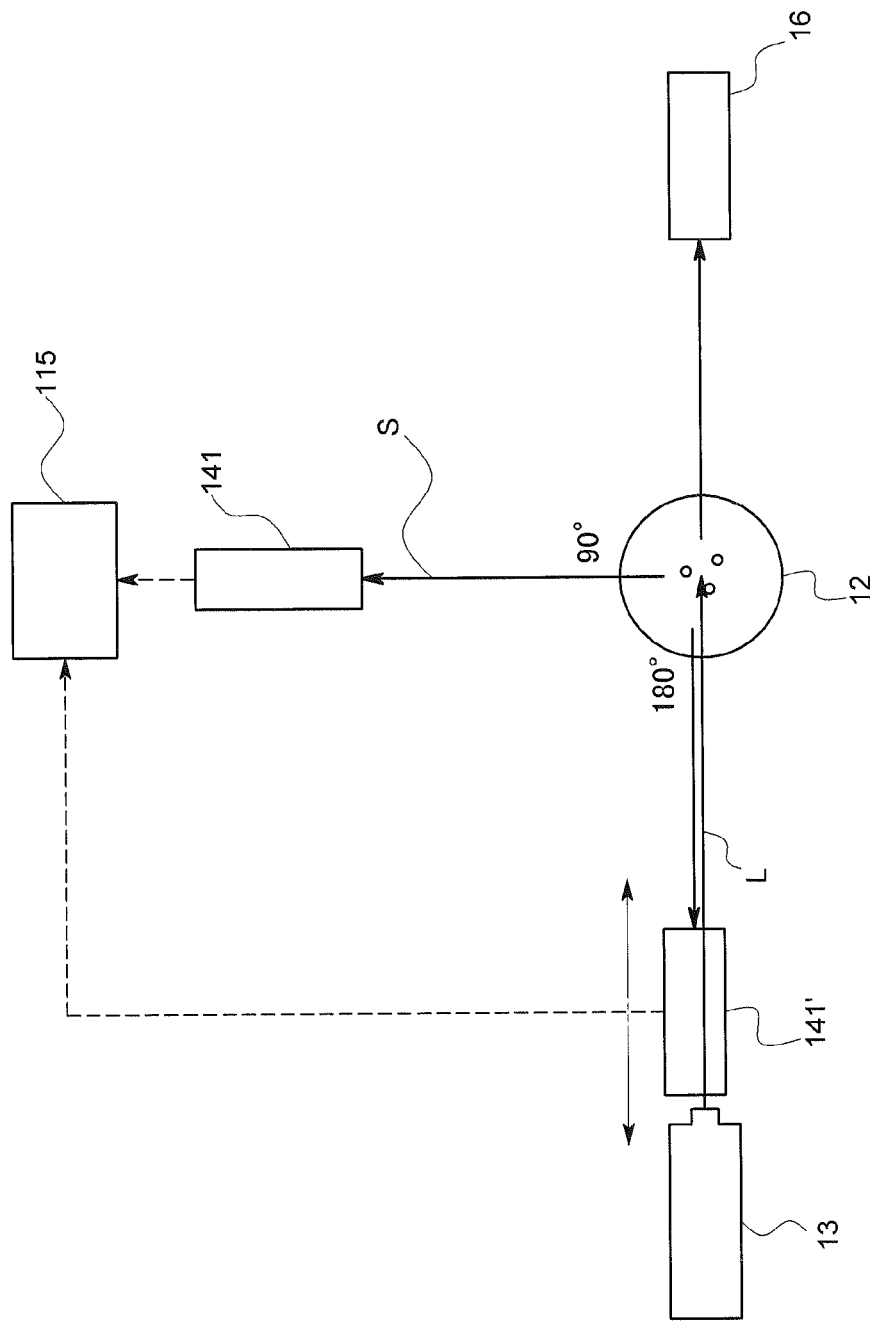
FIG. 13 is a schematic configuration diagram illustrating a particle size measuring mechanism in the same embodiment.

The particle size measuring mechanism includes, as illustrated in FIG. 13, a laser 13, the light receiving parts 141 and 141', a correlator 115, and the transmitted light amount sensor 16. Also, the light receiving part 141' is provided with an unillustrated light receiving position moving mechanism. Specifically, the light receiving position moving mechanism is provided with a rail member that slidably supports the light receiving part 141' back and forth, and operation of the rail member is controlled by a position control part 171.

Also, according to a transmitted light amount of laser light passing through a liquid sample, which is measured by the transmitted light amount sensor 16, in the case where the transmitted light amount is large (a concentration of the liquid sample is low), scattered light S through a light path orthogonal to the laser light L (scattering angle of 90°) is received by the light receiving part 141, whereas in the case where the transmitted light amount is small (the liquid sample concentration is high), scattered light S through a light path substantially overlapping with the laser light L (scattering angle of near 180°, preferably 170 to 175°) is received by the light receiving part 141'.

Further, in the case where the transmittance is extremely low (the liquid sample concentration is extremely high), to be able to receive a sufficient amount of scattered light at the scattering angle of near 180°, the position control part 171 slides the light receiving part 141' through the rail member to control a position (a distance from the cell 12) of the light receiving part 141'.

According to the particle characterization device 11 configured as described, the particle size measuring mechanism is provided with the two light receiving parts 141 and 141', and any rotating mechanism for the light receiving part 141 is not required, so that the particle characterization device 11 can be made compact. In the case of the 180-degree detection, the cross section of the cell 12 is square shaped, and therefore noise can be suppressed from being mixed into the scattered light S.

Note that the third aspect of the present invention is not limited to the above embodiment.

For example, the particle characterization device according to the present invention is only required to be provided with at least a particle size measuring mechanism, and mechanisms for measuring the other various types of physical properties may be appropriately provided as needed.

Also, the rail member slidable back and forth may be provided so as to support the cell 12.

Fourth Aspect of the Present Invention

In the following, one embodiment of a fourth aspect of the present invention is described with reference to the drawings.

Note that, in the following description, different points from the above embodiments according to the third aspect of the present invention are focused on to provide the description.

Figure 14:
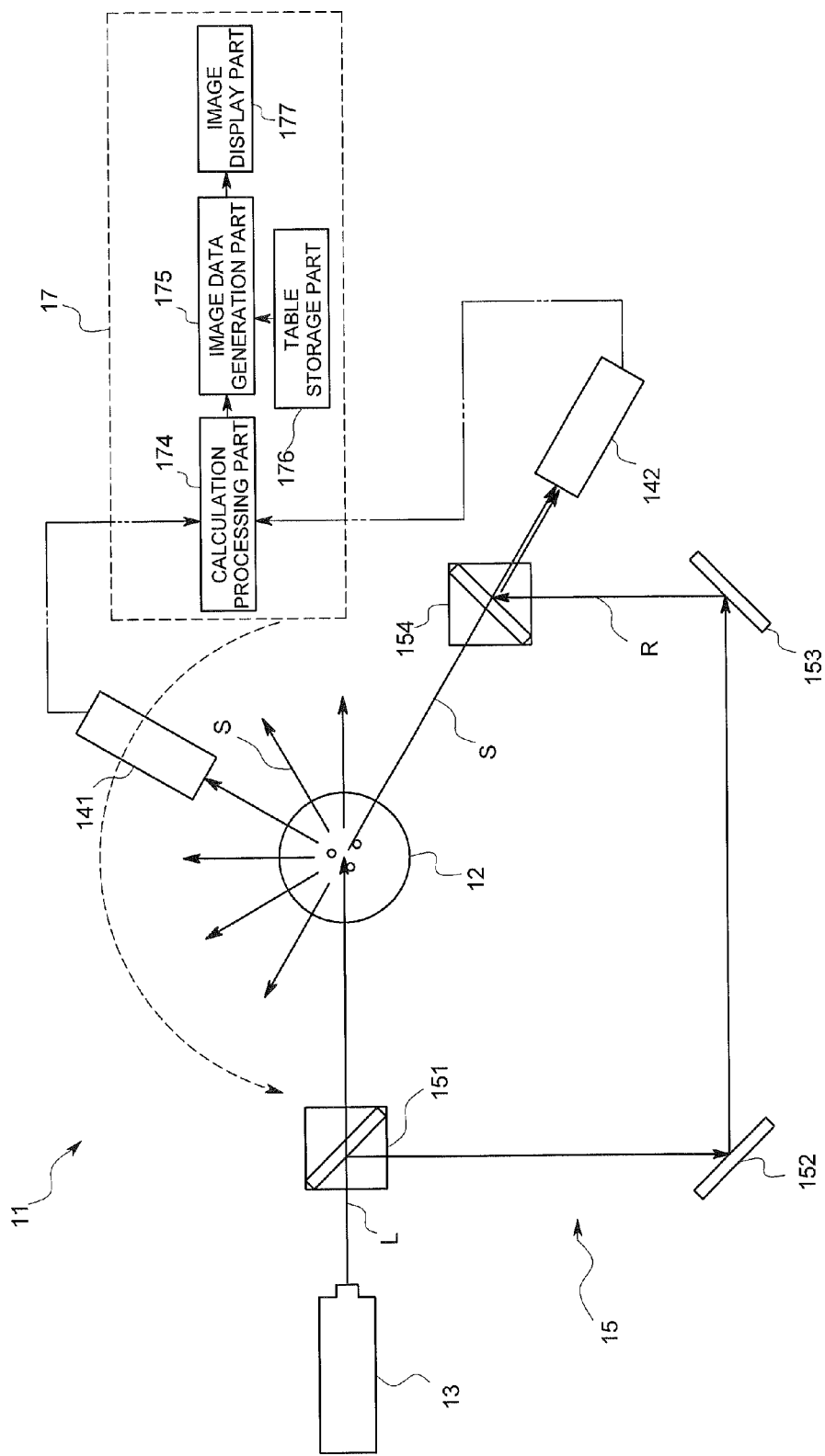
FIG. 14 is a schematic overall diagram illustrating an outline of a particle characterization device according to one embodiment of a fourth aspect of the present invention.

An information processor 17 is configured to further fulfill functions as, as illustrated in FIG. 14, a calculation processing part 174, an image data generation part 175, a table storage part 176, an image display part 177, and the like by a CPU and its peripheral devices that are instructed to collaboratively operate according to a predetermined program stored in a memory.

The calculation processing part 174 receives, directly or through a correlator 115, pulse signals or light intensity signals transmitted from light receiving parts 141 and 142 in each measuring mechanism, and performs predetermined calculation processing to calculate a measurement result.

The image data generation part 175 is one that acquires pieces of data on the measurement results in the respective measuring mechanism from the calculation processing part 174, and on the basis of the measurement results of the various types of physical properties, generates pieces of image data for displaying a particle and an electric field formed around the particle as an image. Note that a size or color of a layer representing the electric field is changed depending on a measurement result of a zeta potential.

Figure 15:
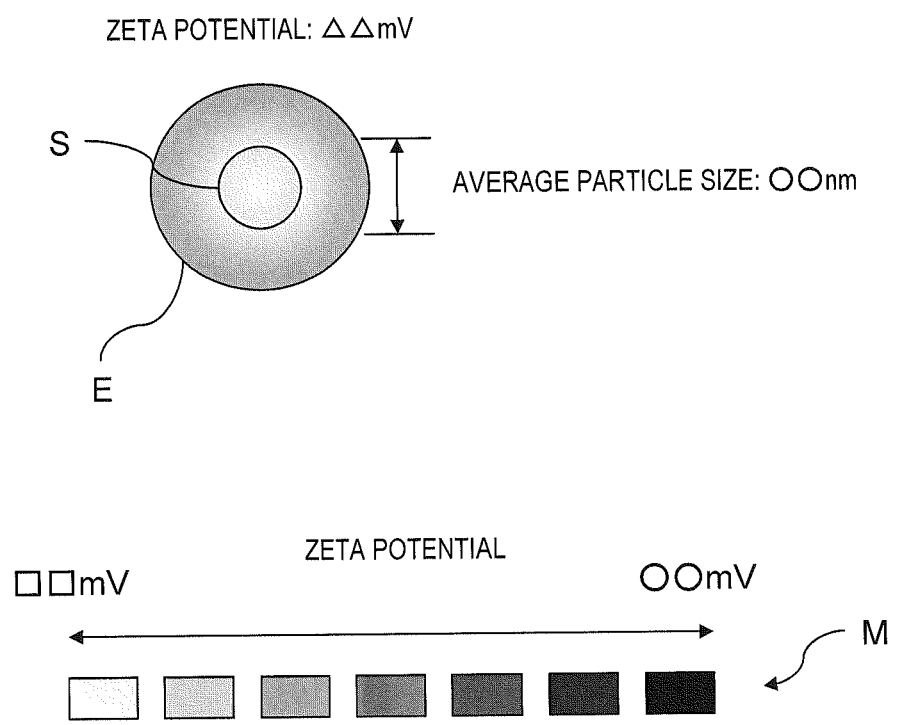
FIG. 15 is a conceptual diagram illustrating an image representing measurement results in the same embodiment.
Figure 16:
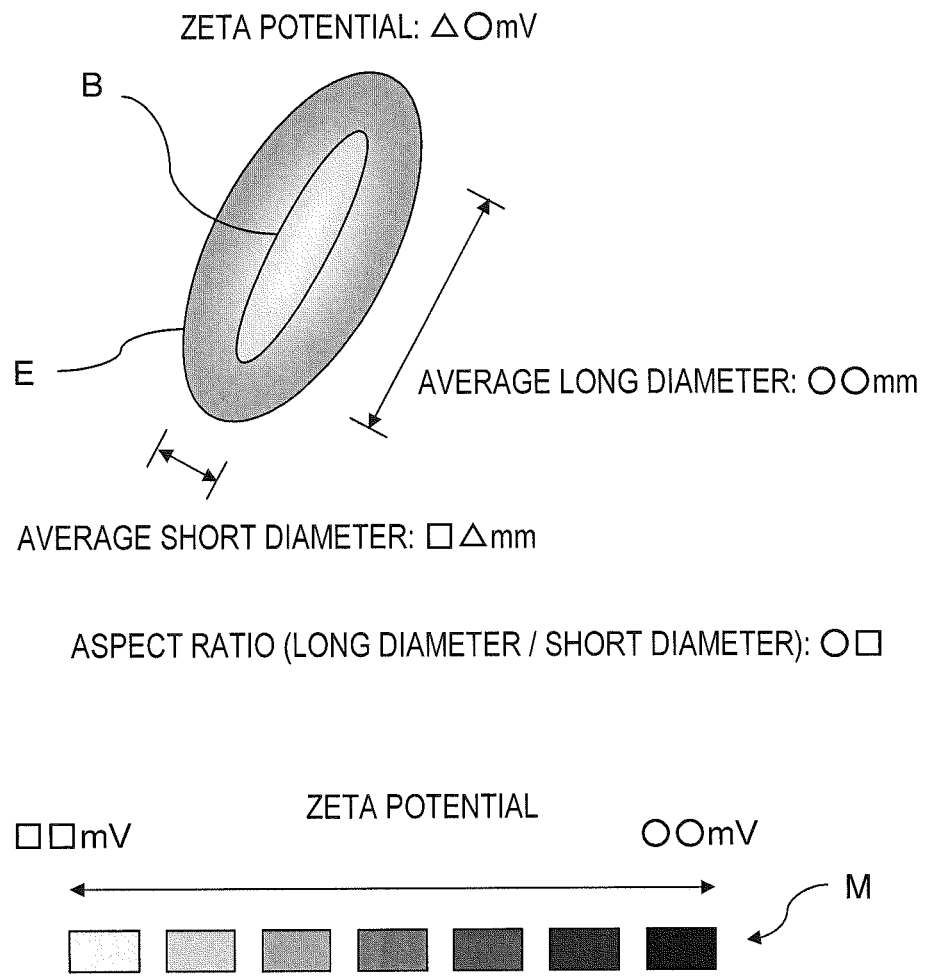
FIG. 16 is a conceptual diagram illustrating an image representing measurement results in the same embodiment.
Figure 17:
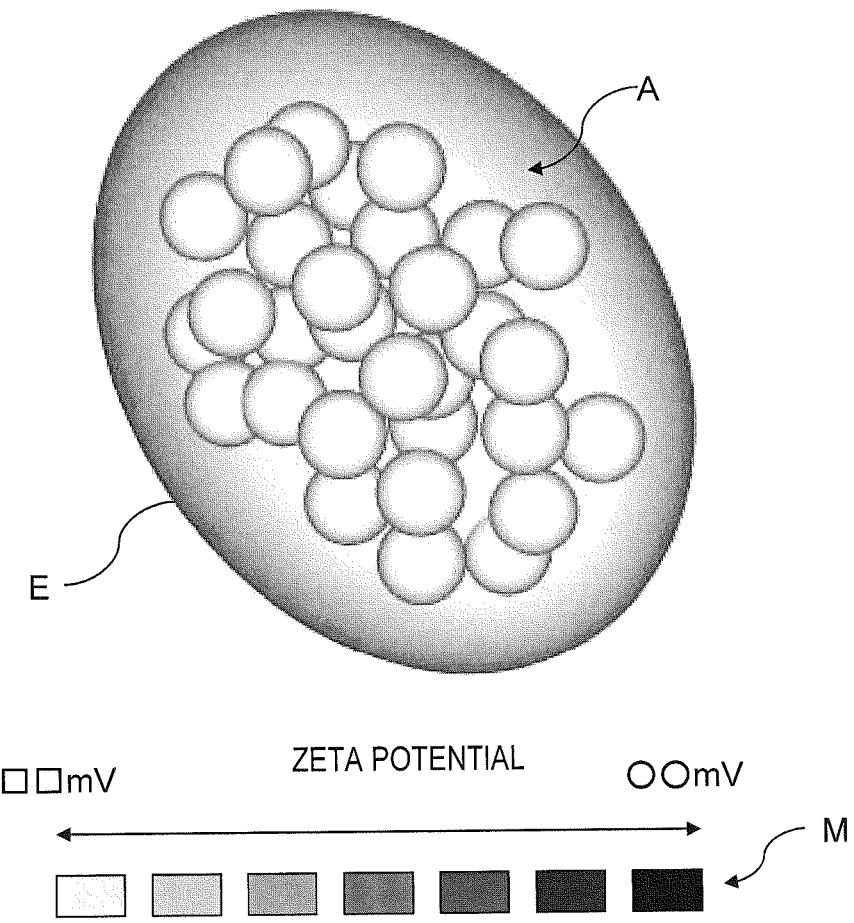
FIG. 17 is a conceptual diagram illustrating an image representing measurement results in the same embodiment.

The image generated by the image data generation part 175 is one in which, as an example of the image is illustrated in FIG. 15, in the circumference (outer edge) of a sphere S having an average particle size of primary particles measured by the particle size measuring mechanism, an electric field E is displayed as a layer with a color being changed on the basis of an average charge amount of the primary particles obtained from the measurement result of the zeta potential by the zeta potential measuring mechanism. Simultaneously with the display of the image, a color sample M corresponding to the measurement result of the zeta potential is also displayed together. Also, in the case where the primary particles or a secondary particle formed by agglomerating the primary particles is rod-like, as illustrated in FIG. 16, average short and long diameters obtained from the measurement results of the shape-related physical property values are displayed together with a rod-like body B such as an ellipsoidal body or a cylinder solid generated according to the shape-related physical property values. Further, as illustrated in FIG. 17, in the case where the primary particles are agglomerated to form the secondary particle A, an agglomeration state is three-dimensionally displayed, for example, how may primary particles of which a particle size has been clarified are agglomerated to form the secondary particle A, which fractal form the primary particles are agglomerated into, and so on. Even in such a case, around the rod-like primary particle B, or the secondary particle A formed into the rod-like shape as the agglomeration result, the electric field E is displayed as a layer with a color or the like being changed on the basis of the average charge amount obtained from the zeta potential measurement result. That is, on the basis of a particle surface shape in the particle image data, data representing the particle size, and zeta potential image data based on the zeta potential measurement result, the electric field is adapted to be displayed on a particle surface as the layer.

The table storage part 176 is one that stores a table in which the zeta potential measurement result and a size or color of the layer representing the electric field are related to each other.

The image display part 177 acquires the pieces of image data generated by the image data generation part 175, and embodies the measurement results of the various types of physical properties to display them as an image.

Figure 18:
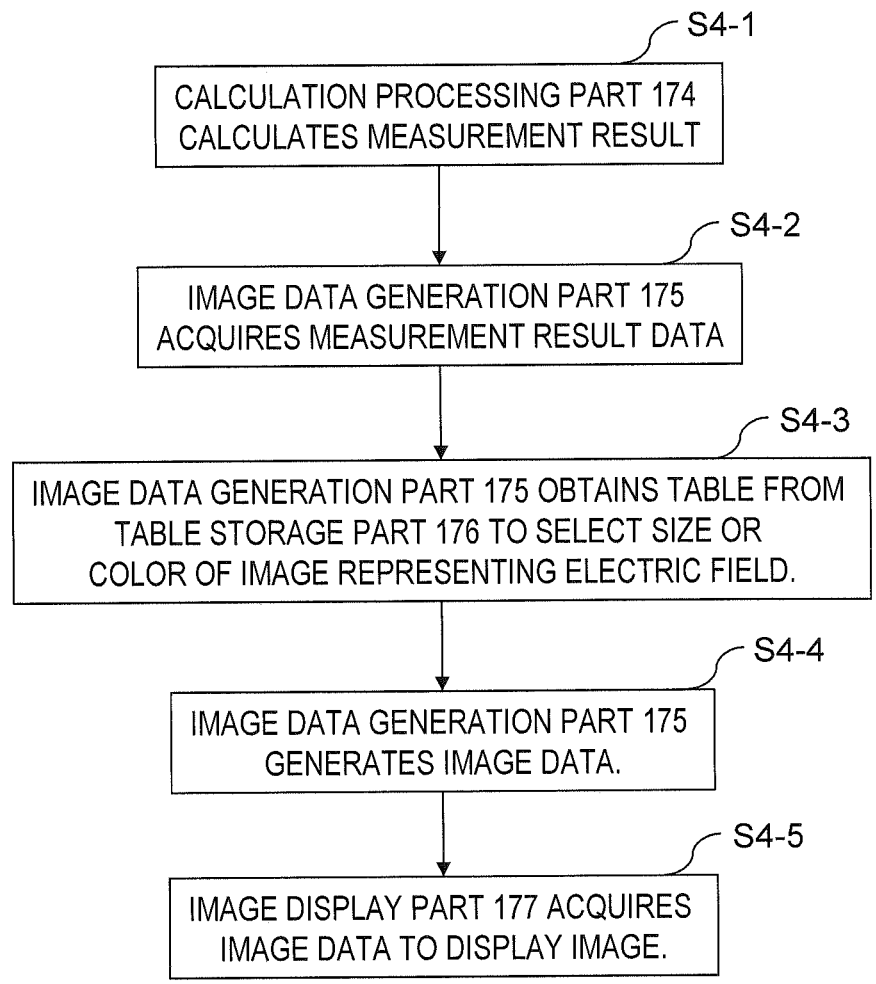
FIG. 18 is a chart illustrating an image generating procedure in the same embodiment.

Next, a procedure for displaying results measured in the respective measuring mechanism as an image is described with reference to a flowchart in FIG. 18.

First, the calculation processing part 174 receives signals transmitted from the light receiving part 141 and 142 directly or through the correlator 115 or the like, and performs the predetermined calculation processing to calculate measurement results of the various types of physical properties (Step S4-1).

Then, the image generation part 175 acquires pieces of data on the measurement results of the various types of physical properties from the calculation processing part 174 (Step S4-2).

Subsequently, the image data generation part 175 acquires, from the table storage part 176, the table storing the zeta potential measurement result and a size or color of an image representing an electric field formed around a particle as a pair, and selects the size or color of the image corresponding to the zeta potential measurement result (Step S4-3).

After that, the image data generation part 175 generates image data for displaying the particle and the electric field formed around the particle as the image on the basis of the measured physical properties (Step S4-4). Note that the size or color of the layer representing the electric field is changed depending on the zeta potential measurement result.

The image display part 177 acquires the image data generated in the image data generation part 175, and as the image, outputs the results measured by the respective measuring mechanisms (Step S4-5).

According to the particle characterization device 11 configured as described according to the present embodiment, on the basis of the measurement results obtained as numerical values and the like, such as the shape-related physical property values and particle size, the image of the particle in the liquid sample is generated, so that from the embodied measurement results, the state of the particle in the liquid sample can be sterically and sensuously figured out and even one unfamiliar with the measurements can easily understand the measurement results. Also, the layer representing the electric field is displayed with a size or color being changed depending on the zeta potential measurement result, so that the zeta potential measurement result can be easily figured out at a glance and an understanding level is improved. In the circumference (outer edge) of the particle in the pieces of particle image data obtained on the basis of the measurement results of the shape-related physical property values such as the aspect ratio and agglomeration level, and particle size, data on the electric field (zeta potential image data) obtained on the basis of the zeta potential measurement result is displayed, so that even one unfamiliar with the measurements is likely to understand a state of microparticles in a solution. Further, the measurements of the various types of physical properties are performed in the liquid, and therefore a state of the particles, which cannot be known from a dry state observation image by an electron microscope such as a SEM, can be specifically figured out.

Note that the fourth aspect of the present invention is not limited to the above embodiment.

For example, in FIGS. 15 to 17, the layer representing the electric field is adapted to be changed in color depending on the zeta potential measurement result; however, the electric field may be displayed as a layer in the outer edge of the particle S, A, or B such that depending on the zeta potential measurement result, a size of the layer representing the electric field is changed, and any one or both of the size and the color may be selectable.

The particle characterization device according to the fourth aspect of the present invention can also generate data for displaying a particle surface shape and a particle size as an image on the basis of measurement result data in the molecular weight measuring mechanism, in addition to the shape-related physical property value measuring mechanism and the particle size measuring mechanism. On the other hand, not all the measuring mechanisms provided in the particle characterization device 11 of the above embodiments may be provided, and for example, the molecular weight measuring mechanism may not be provided.

Besides, it should be appreciated that the present invention can be variously modified without departing from the scope thereof.

INDUSTRIAL APPLICABILITY

According to the first aspect of the present invention having such a configuration, when a light intensity is detected, light is appropriately attenuated by the light attenuating means, and thereby even with the single light detecting means, the physical properties can be measured with high accuracy over a wide range. Also, the number of required optical elements is small, so that a transmittance and stray light can be prevented from being reduced and occurring, respectively, and also as an optical element that is rotationally driven for measurements, the exit side polarizer is only required, so that the number of adjustment places can be reduced as much as possible to improve operability and measurement accuracy.

Also, according to the second aspect of the present invention, because the correction parameters are set for the respective measurement angle positions, light amount variations or the like due to mechanical errors at the respective measurement angle positions can be corrected with use of the correction parameters, and therefore the physical properties related to a particle shape can be measured with high accuracy. Also, without requiring a complicated mechanism, realization with a simple configuration is possible.

Further, according to the third aspect of the present invention, depending on a concentration of the liquid sample, the light receiving position for scattered light at the time of the particle size measurement can be moved to constantly receive the scattered light at an appropriate position, and therefore the particle size measurement can be performed with high accuracy. Also, by providing the shape-related physical property measuring mechanism, zeta potential measuring mechanism, and the like, even in the case of a trace amount of liquid sample, the various physical properties can be efficiently measured only with the one device.

Still further, according to the fourth aspect of the present invention, measurement results of the various types of physical properties are displayed as an image together with numerical values and distribution, so that even one who measures the various types of physical properties of particles for the first time, or does not have so many opportunities to perform the measurements can figure out a particle's state of being in a liquid as a specific image, and therefore an understanding level for the measurement results of the various types of physical properties is improved.

REFERENCE SIGNS LIST

1: Particle characterization device
L1: Primary light (Laser light)
L2: Scattered light
2: Illumination optical system mechanism
21: Light source (Semiconductor laser)
23: Light attenuating means
231: ND filter
232: Filter changing mechanism
232a: Rotational holding plate
24: Incident side polarizer
25: Incident side ¼ wavelength plate
3: Light receiving optical system mechanism
31: Light detecting means
33: Exit side ¼ wavelength plate
34: Exit side polarizer
4: Cell
51: Angle control part
52: Light attenuation rate control part
53: Physical property calculation part
54: Particle size distribution calculation part
55: Correction parameter storage part
11: Particle characterization device
12: Cell
13: Light source
162: Image data generation part
S, B, A: Particle(s)
E: Electric field

The invention claimed is:

1. A particle characterization device comprising:
a transparent cell that contains a sample in which a micro particle is dispersed in a dispersion medium;
an illumination optical system mechanism having an incident side polarizer and an incident side ¼ wavelength plate that are sequentially provided on a light path from a light source to the cell arrived by primary light emitted from the light source;
a light receiving optical system mechanism that has: light detecting means adapted to detect an intensity of received light; and an exit side ¼ wavelength plate and an exit side polarizer that are sequentially provided on a light path through which secondary light scattered by the particle in the cell travels to the light intensity detecting means, and is rotatably supported around the cell;
light attenuating means adapted to, without changing a polarization state of the primary light or the secondary light, attenuate the light with being able to change a light attenuation rate;
an angle control part that controls the light receiving optical system mechanism to a plurality of rotational angle positions, and at each of the rotational angle positions, controls a polarization angle of the exit side polarizer to a plurality of angles;
a light attenuation rate control part that controls the light attenuation rate by the light attenuating means such that a detected light intensity at each of the polarization angles at each of the rotational angle positions falls within a measurement range of the light detecting means; and
a physical property calculation part that calculates a physical property of the particle on a basis of a light attenuation rate at each of the polarization angles at each of the rotational angle positions and a detected light intensity after the light attenuation.

2. The particle characterization device according to claim 1, wherein
the physical property calculation part calculates physical property values related to a particle shape such as an aspect ratio and an agglomeration level.

3. The particle characterization device according to claim 1, wherein
the light attenuating means includes: a plurality of ND filters respectively having different light attenuation rates; and a filter changing mechanism that selectively inserts any of the ND filters into the light path of the primary light or the secondary light.

4. The particle characterization device according to claim 2, wherein
the filter changing mechanism includes a rotational holding plate arranged with the plurality of ND filters in a circumferential part, and is configured such that by rotating the rotational holding plate, any of the ND filters is positioned on the light path of the primary light or the secondary light.

5. The particle characterization device according to claim 1, wherein
the light receiving optical system mechanism is configured to be able to be arranged on an extended line of the primary light transmitting through the cell to measure an intensity of transmitted light having transmitted through the cell by the light detecting means.

6. The particle characterization device according to claim 1, further comprising
a particle size distribution calculation part that, on a basis of a fluctuation of a light intensity detected by the light detecting means, calculates a particle size distribution.

7. The particle characterization device according to claim 6, wherein
the angle control part changes the rotational angle position of the light receiving optical system mechanism depending on a particle concentration in the sample when the particle size distribution is measured by the particle size distribution calculation part.

8. A particle characterization device comprising:
a transparent cell that contains a sample in which a micro particle is dispersed in a dispersion medium;
an illumination optical system mechanism having an incident side polarizer and an incident side ¼ wavelength plate that are sequentially provided on a light path from a light source to the cell arrived by primary light emitted from the light source;
a light receiving optical system mechanism that has: light detecting means adapted to detect an intensity of received light; and an exit side ¼ wavelength plate and an exit side polarizer that are sequentially provided on a light path through which secondary light scattered by the particle in the cell travels to the light intensity detecting means, and is rotatably supported around the cell;
an angle control part that rotates the light receiving optical system mechanism around the cell to control the light receiving optical system mechanism to a plurality of rotational angle positions, and at each of the rotational angle positions, controls a polarization angle of the exit side polarizer to a plurality of angles;
a correction parameter storage part that stores a correction parameter for a detected light intensity at each of the measurement angle positions;
a physical property calculation part that, on a basis of a sample detected light intensity corresponding to a detected light intensity at each of the polarization angles at each of the measurement angle positions and the correction parameter, calculates a physical property related to a shape of the particle
light attenuating means adapted to, without changing a polarization state of the primary light or the secondary light, attenuate the light with being able to change an amount of the light; and
a light attenuation rate control part that controls a light attenuation rate by the light attenuating means such that the detected light intensity at each of the polarization angles at each of the measurement angle positions falls within a measurement range of the light detecting means.

9. A particle characterization device that has: a cell that contains a liquid sample in which a particle is dispersed; a light source that irradiates the particle in the cell with light; and a light receiving part that receives scattered light emitted from the particle irradiated with the light, and on a basis of scattered light information serving as information on the scattered light, measures a physical property of the particle, the particle characterization device comprising at least:
a particle size measuring mechanism that uses a dynamic light scattering method to measure a particle size of the particle; and a transmitted light amount measuring mechanism that measures, among lights irradiated from the light source, an amount of transmitted light having transmitted through the liquid sample contained in the cell, the particle characterization device further comprising:
a light receiving position moving mechanism that on a basis of the amount of the transmitted light, moves a light receiving position for the scattered light in the particle size measuring mechanism.

10. The particle characterization device according to claim 9, wherein
the light receiving position moving mechanism includes a rotating mechanism and/or a sliding mechanism.

11. The particle characterization device according to claim 9, further comprising:
a shape-related physical property value measuring mechanism that uses a polarizer to irradiate the liquid sample with lights having different polarization patterns, and on a basis of transmittances for the lights and a scattered light intensity ratio at a predetermined scattering angle, measures a shape-related physical property value of the particle, wherein
the transmitted light amount measuring mechanism is the shape-related physical property value measuring mechanism.

12. The particle characterization device according to claim 11, further comprising a zeta potential measuring mechanism, the particle characterization device comprising:
a measurement control part that controls the respective measuring mechanisms such that respective physical property values of the shape-related physical property value, the particle size, and a zeta potential are measured in this order.

* * * * *